(12) United States Patent  
Sloan et al.

(10) Patent No.: US 12,220,558 B2
(45) Date of Patent: Feb. 11, 2025

(54) CONTINUOUS GLUCOSE MONITORING SYSTEM

(71) Applicant: ABBOTT DIABETES CARE INC., Alameda, CA (US)

(72) Inventors: Mark Sloan, Redwood City, CA (US); Marc B. Taub, Mountainview, CA (US); Charles Wei, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 17/567,684

(22) Filed: Jan. 3, 2022

(65) Prior Publication Data

US 2022/0118180 A1  Apr. 21, 2022

Related U.S. Application Data

(60) Continuation of application No. 16/560,497, filed on Sep. 4, 2019, now Pat. No. 11,213,622, which is a
(Continued)

(51) Int. Cl.
*G08B 21/02* (2006.01)
*A61B 5/00* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
USPC .............. 340/573.1, 538.13, 539.12, 539.11, 340/539.22, 545.3, 555, 588, 691.6, 691.3
See application file for complete search history.

(56) References Cited

U.S. PATENT DOCUMENTS

| 5,569,186 A | 10/1996 | Lord et al. |
| 5,665,065 A | 9/1997 | Colman et al. |

(Continued)

FOREIGN PATENT DOCUMENTS

| WO | WO 99/56613 | 11/1999 |
| WO | WO 2004/009161 | 1/2004 |

(Continued)

OTHER PUBLICATIONS

Exhibit CP-3, Expert Report of Dr. Cesar C. Palerm, Sep. 20, 2022: In Vivo Glucose Sensing, Chemical Analysis, A Series of Monographs on Analytical Chemistry and Its Applications, vol. 174, Wiley (2010).

(Continued)

*Primary Examiner* — Daniel Previl
(74) *Attorney, Agent, or Firm* — Baker Botts L.L.P.

(57) ABSTRACT

Methods and systems for delaying alarms that include detecting an analyte level using an analyte sensor; and delaying the annunciation of an analyte alarm after the analyte level crosses an analyte threshold, wherein the delay is based on one or both of (1) a magnitude of difference between the analyte level and the analyte threshold and (2) a duration of time in which the analyte level has crossed the analyte threshold.

26 Claims, 3 Drawing Sheets

Related U.S. Application Data continuation of application No. 15/282,688, filed on Sep. 30, 2016, now abandoned, which is a division of application No. 14/076,109, filed on Nov. 8, 2013, now abandoned, which is a continuation of application No. 12/785,144, filed on May 21, 2010, now Pat. No. 8,597,274.

(60) Provisional application No. 61/180,649, filed on May 22, 2009.

(51) Int. Cl.

| | | |
|---|---|---|
| *A61B 5/145* | (2006.01) | |
| *A61M 5/142* | (2006.01) | |
| *A61M 5/172* | (2006.01) | |
| *G08B 21/04* | (2006.01) | |
| *G08B 21/18* | (2006.01) | |
| *G16H 20/17* | (2018.01) | |
| *G16H 50/50* | (2018.01) | |
| *G16H 40/67* | (2018.01) | |

(52) U.S. Cl.
CPC ............ *A61B 5/746* (2013.01); *A61M 5/142* (2013.01); *G08B 21/0453* (2013.01); *G08B 21/182* (2013.01); *G16H 20/17* (2018.01); *G16H 50/50* (2018.01); *A61M 2005/14296* (2013.01); *A61M 2205/18* (2013.01); *A61M 2205/3569* (2013.01); *A61M 2205/52* (2013.01); *A61M 2230/201* (2013.01); *G16H 40/67* (2018.01)

(56) References Cited

U.S. PATENT DOCUMENTS

| | | | |
|---|---|---|---|
| 5,822,715 A | 10/1998 | Worthington et al. | |
| 6,175,752 B1 | 1/2001 | Say et al. | |
| 6,544,212 B2 | 4/2003 | Galley et al. | |
| 6,923,763 B1 | 8/2005 | Kovatchev et al. | |
| 7,278,983 B2 | 10/2007 | Ireland et al. | |
| 7,976,492 B2 * | 7/2011 | Brauker ............... | G16H 20/17 604/503 |
| 8,073,008 B2 | 12/2011 | Mehta et al. | |
| 8,282,549 B2 | 10/2012 | Brauker et al. | |
| 8,417,312 B2 * | 4/2013 | Kamath ............. | A61B 5/14532 600/347 |
| 8,597,274 B2 * | 12/2013 | Sloan ................ | A61B 5/14532 604/504 |
| 10,980,461 B2 | 4/2021 | Simpson et al. | |
| 11,213,622 B2 * | 1/2022 | Sloan ..................... | G16H 50/50 |
| 2002/0045808 A1 | 4/2002 | Ford et al. | |
| 2003/0114836 A1 | 6/2003 | Estes et al. | |
| 2003/0163789 A1 | 8/2003 | Blomquist | |
| 2005/0038332 A1 | 2/2005 | Saidara et al. | |
| 2005/0171513 A1 | 8/2005 | Mann et al. | |
| 2005/0195930 A1 | 9/2005 | Spital et al. | |
| 2006/0087655 A1 | 4/2006 | Augustine et al. | |
| 2006/0173406 A1 | 8/2006 | Hayes et al. | |
| 2006/0276771 A1 | 12/2006 | Galley et al. | |
| 2007/0052965 A1 | 3/2007 | Pesach et al. | |
| 2007/0078314 A1 | 4/2007 | Grounsell et al. | |
| 2007/0106135 A1 | 5/2007 | Sloan et al. | |
| 2007/0118030 A1 | 5/2007 | Bruce et al. | |
| 2007/0149874 A1 | 6/2007 | Say et al. | |
| 2007/0170054 A2 | 7/2007 | Wilsey | |
| 2007/0173761 A1 | 7/2007 | Kanderian, Jr. et al. | |
| 2007/0179370 A1 | 8/2007 | Say et al. | |
| 2007/0208244 A1 | 9/2007 | Brauker et al. | |
| 2007/0213657 A1 * | 9/2007 | Jennewine ............. | G16H 20/17 604/67 |
| 2007/0235331 A1 | 10/2007 | Simpson et al. | |
| 2008/0119710 A1 | 5/2008 | Reggiardo et al. | |
| 2008/0149821 A1 | 6/2008 | Senko | |
| 2008/0172026 A1 | 7/2008 | Blomquist | |
| 2008/0172030 A1 | 7/2008 | Blomquist | |
| 2008/0172031 A1 | 7/2008 | Blomquist | |
| 2008/0235053 A1 | 9/2008 | Ray et al. | |
| 2008/0262469 A1 | 10/2008 | Brister et al. | |
| 2008/0300572 A1 | 12/2008 | Rankers et al. | |
| 2008/0306444 A1 * | 12/2008 | Brister ............... | A61B 5/14546 604/131 |
| 2009/0006129 A1 | 1/2009 | Thukral et al. | |
| 2009/0055149 A1 | 2/2009 | Hayter et al. | |
| 2009/0114811 A1 | 5/2009 | Landgraf | |
| 2009/0192366 A1 | 7/2009 | Mensinger et al. | |
| 2009/0192380 A1 | 7/2009 | Shariati et al. | |
| 2009/0216102 A1 | 8/2009 | Say et al. | |
| 2009/0221890 A1 | 9/2009 | Saffer et al. | |
| 2009/0254037 A1 | 10/2009 | Bryant et al. | |
| 2009/0275887 A1 | 11/2009 | Estes | |
| 2010/0017141 A1 | 1/2010 | Campbell et al. | |
| 2010/0049164 A1 | 2/2010 | Estes | |
| 2010/0161236 A1 | 6/2010 | Cohen et al. | |
| 2010/0191472 A1 | 7/2010 | Doniger et al. | |
| 2010/0198314 A1 | 8/2010 | Wei | |
| 2010/0280441 A1 | 11/2010 | Wilinska et al. | |
| 2011/0077494 A1 | 3/2011 | Doniger et al. | |
| 2011/0124996 A1 | 5/2011 | Reinke et al. | |
| 2014/0039383 A1 | 2/2014 | Dobbles et al. | |
| 2014/0052095 A1 * | 2/2014 | Dobbles ............ | A61M 5/14244 604/504 |
| 2014/0350371 A1 | 11/2014 | Blomquist et al. | |
| 2015/0094914 A1 | 4/2015 | Abreu | |

FOREIGN PATENT DOCUMENTS

| | | |
|---|---|---|
| WO | WO 2006/079867 | 8/2006 |
| WO | WO 2008/030347 | 3/2008 |
| WO | WO 2008/151452 | 12/2008 |
| WO | WO 2009/049252 | 4/2009 |
| WO | WO 2009/146119 | 12/2009 |
| WO | WO 2011/041007 | 4/2011 |
| WO | WO 2011/060923 | 5/2011 |

OTHER PUBLICATIONS

Exhibit CP-4, Expert Report of Dr. Cesar C. Palerm, Sep. 20, 2022: Animas® Vibe™, the First Integrated Offering from Animas Corporation and Dexcom, Inc., Receives European CE Mark Approval (2011).

Exhibit CP-6, Second Expert Report of Dr. Cesar C. Palerm, Oct. 21, 2022: Bailey, et al., Reduction in Hemoglobin A1c with Real-Time Continuous Glucose Monitoring: Results from a 12-Week Observational Study, Diabetes Technology & Therapeutics, vol. 9, No. 3, pp. 203-210 (2007).

Exhibit CP-7, Second Expert Report of Dr. Cesar C. Palerm, Oct. 21, 2022: Garg, et al., Improvement in Glycemic Excursions With a Transcutaneous, Real-Time Continuous Glucose Sensor, Diabetes Care, vol. 29, No. 1, pp. 44-50 (2006).

Exhibit CP-8, Second Expert Report of Dr. Cesar C. Palerm, Oct. 21, 2022: Garg, et al., Relationship of Fasting and Hourly Blood Glucose Levels to HbA1c Values, Diabetes Care, vol. 29, No. 12, pp. 2644-2649 (2006).

Exhibit CP-9, Second Expert Report of Dr. Cesar C. Palerm, Oct. 21, 2022: Welcome to Your FreeStyle Libre System, In-Service Guide, Abbott (2017).

Exhibit CP-10, Second Expert Report of Dr. Cesar C. Palerm, Oct. 21, 2022: Standards of Medical Care in Diabetes-2009, American Diabetes Association, Diabetes Care, vol. 32, Supplement 1, pp. S13-S61 (2009).

Exhibit No. 23, to the Expert Report of Professor Nick Oliver, Sep. 20, 2022: CGMS® System Gold™ Continuous Glucose Monitoring Overview, Medtronic MiniMed (2004).

Exhibit No. 20, to the Expert Report of Professor Nick Oliver, Sep. 20, 2022: Continuous Glucose Sensors: Continuing Questions about Clinical Accuracy, J Diabetes Sci Technol vol. 1, Issue 5, pp. 669-675 (2007).

(56) References Cited

OTHER PUBLICATIONS

Exhibit No. 19, to the Expert Report of Professor Nick Oliver, Sep. 20, 2022: Glucose Concentrations of Less Than 3.9 mmol/L (54 mg/dL) Should be Reported in Clinical Trials: A Joint Position Statement of the America Diabetes Association and the European Association for the Study of Diabetes, Diabetes Care, vol. 40, pp. 155-157 (2017).
Exhibit No. 18, to the Expert Report of Professor Nick Oliver, Sep. 20, 2022: Aleppo, et al., REPLACE-BG: A Randomized Trial Comparing Continuous Glucose Monitoring With and Without Routine Blood Glucose Monitoring in Adults With Well-Controlled Type 1 Diabetes, Diabetes Care, vol. 40, pp. 538-545 (2017).
Exhibit No. 17, to the Expert Report of Professor Nick Oliver, Sep. 20, 2022: Diabetes (type 1), NIHR (2011).
Exhibit No. 16, to the Expert Report of Professor Nick Oliver, Sep. 20, 2022: Pickup, et al., Glycaemic control in type 1 diabetes during real time continous glucose monitoring compared with self minotoring of blood glucose: meta-analysis of randomised controlled trials using individual patient date, BMJ (2011).
Exhibit No. 15, to the Expert Report of Professor Nick Oliver, Sep. 20, 2022: Oxford Textbook of Endocrinology and Diabetes (2011).
Exhibit No. 14, to the Expert Report of Professor Nick Oliver, Sep. 20, 2022: Type 1 diabetes: diagnosis and management of type 1 diabetes in children, young people and adults, Clinical Guideline 15, NHS, National Institute for Clinical Excellence (2004).
Exhibit No. 13, to the Expert Report of Professor Nick Oliver, Sep. 20, 2022: Training in flexible, intensive, insulin mangement to enable dietrary freedom in people with type 1 diabetes: dose adjustment for normal eating (DAFNE) randomised controlled trial, BMJ, vol. 325 (2002).
Exhibit No. 12, to the Expert Report of Professor Nick Oliver, Sep. 20, 2022: Modern Standards and Service Models, Diabetes, National Service Framework for Diabetes: Standards, Department of Health (2000).
Exhibit No. 11, to the Expert Report of Professor Nick Oliver, Sep. 20, 2022: The Effect of Intensive Treatment of Diabetes on the Development and Progression of Long-Term Complications in Insulin-Dependent Diabetes Mellitus, The New England Journal of Medicine, vol. 329, No. 14 (1993).
Exhibit No. 10, to the Expert Report of Professor Nick Oliver, Sep. 20, 2022: Type 1 Diabetes Research Roadmap, Identifying the strengths and weaknesses, gaps and opportunities of UK type 1 diabetes research; clearing a path to the cure, JDRF Improving Lives. Curing Type 1 Diabetes. Join us in finding the cure for type 1 diabetes (2013).
Exhibit No. 9, to the Expert Report of Professor Nick Oliver, Sep. 20, 2022: Guideline on clinical investigation of medicinal products in the treatment or prevention of diabetes mellitus, European Medicines Agency, Science Medicines Health (2012).
Exhibit No. 8, to the Expert Report of Professor Nick Oliver, Sep. 20, 2022: Oxford Textbook of Endocrinology and Diabetes (2011).
Exhibit No. 7, to the Expert Report of Professor Nick Oliver, Sep. 20, 2022: Cryer, Preventing hypoglycaemia: what is the appropriate glucose alert value?, Diabetologia, vol. 52, pp. 35-37 (2009).
Exhibit No. 6, to the Expert Report of Professor Nick Oliver, Sep. 20, 2022: Frier, Defining hypoglycaemia: what level has clinical relevance?, Diabetologia, vol. 52, pp. 31-34 (2009).
Exhibit No. 5, to the Expert Report of Professor Nick Oliver, Sep. 20, 2022: Swinnen, et al., Changing the glucose cut-off values that define hypoglycaemia has a major effect on reported frequencies of hypoglycaemia, Diabetologis, vol. 52, pp. 38-41 (2009).
Exhibit No. 4, to the Expert Report of Professor Nick Oliver, Sep. 20, 2022: Amiel, et al., Review Article, Hypoglycaemia in Type 2 diabetes, Diabetic Medicine, vol. 25, pp. 245-254 (2008).
Exhibit No. 3, to the Expert Report of Professor Nick Oliver, Sep. 20, 2022: Defining and Reporting Hypoglycemia in Diabetes, Diabetes Care, vol. 28, No. 5, pp. 1245-1249 (2005).
Exhibit No. 2, to the Expert Report of Professor Nick Oliver, Sep. 20, 2022: Committee for Proprietary Medicinal Products (CPMP), Note for Guidance on Clinical Investigation of Medicinal Products in the Treatment of Diabetes Mellitus, EMEA, The European Agenecy for the Evaluation of Medicinal Products (2002).
Exhibit No. 28, to the Expert Report of Professor Nick Oliver, Sep. 20, 2022: FreeStyle Navigator II, Continuous Glucose Monitoring System, User's Manual, Abbott (2011-2013).
Exhibit No. 27, to the Expert Report of Professor Nick Oliver, Sep. 20, 2022: FreeStyle Navigator, Continuous Glucose Monitoring System, User Guide, Abbott (2008, 2010).
Exhibit No. 26, to the Expert Report of Professor Nick Oliver, Sep. 20, 2022: CGMS® iPro™ Continuous Glucose Recorder, User Guide, Medtronic MiniMed (2007).
Exhibit No. 25, to the Expert Report of Professor Nick Oliver, Sep. 20, 2022: Guardian® REAL-Time, Continuous Glucose Monitoring System, User Guide, Medtronic MiniMed (2006).
Exhibit No. 24, to the Expert Report of Professor Nick Oliver, Sep. 20, 2022: GlucoWatch G2, Automatic Glucose Biographer and Auto Sensors (2002).
Exhibit No. 20, to the Expert Report of Professor Nick Oliver, Sep. 20, 2022: Continuous Glucose Sensors: Continuing Questions about Clinical Accuracy, Journal of Diabetes Science and Technology, vol. 1, Issue 5, pp. 669-675 (2007).
Exhibit No. 29, to the Expert Report of Professor Nick Oliver, Sep. 20, 2022: Dexcom G4, Continuous Glucose Monitoring System, User's Guide (2013).
Exhibit No. 31, to the Expert Report of Professor Nick Oliver, Sep. 20, 2022: Revised Specification for EP625.
Exhibit No. 32, to the Expert Report of Professor Nick Oliver, Sep. 20, 2022: Puhr, et al., Real-World Hypoglycemia Avoidance with a Predictive Low Glucose Alert Does Not Depend on Frequent Screen Views, Journal of Diabetes Science and Technology, vol. 14(1), pp. 83-86 (2020).
Exhibit No. 33, to the Expert Report of Professor Nick Oliver, Sep. 20, 2022: Rilstone, et al., The impact of CGM with a predictive hypoglycaemia alert function on hypoglycaemia in physical activity for peoper with type 1 diabetes: PACE study (2022).
Exhibit No. 34, to the Expert Report of Professor Nick Oliver, Sep. 20, 2022: FreeStyle Libre 2, Flash Glucose Monitoring System, User's Manual, Abbott (2019-2021).
Exhibit No. 35, to the Expert Report of Professor Nick Oliver, Sep. 20, 2022: FreeStyle Libre 2, Flash Glucose Monitoring System, User's Manual, Abbott (2022).
Exhibit No. 30, to the Expert Report of Professor Nick Oliver, Sep. 20, 2022: Revised Specification for US 2007/208244A1.
Exhibit No. 22, to the Expert Report of Professor Nick Oliver, Sep. 20, 2022: Innovation Milestones, et al.
Exhibit No. 21, to the Expert Report of Professor Nick Oliver, Sep. 20, 2022: DeVries, Glucose Sensing Issues for the Artificial Pancreas, Journal of Diabetes Science and Technology, vol. 2, Issue 4, pp. 732-734 (2008).
Exhibit No. 37, to the Second Expert Report of Professor Nick Oliver, Oct. 21, 2022: Oliver, et al., Review Article, Glucose sensors, a review of current and emerging technology, Diabetic Medicine, vol. 26, pp. 197-210 (2009).
U.S. Appl. No. 16/560,497 (U.S. Pat. No. 11,213,622) filed Sep. 4, 2019 (Jan. 4, 2022).
U.S. Appl. No. 15/282,688 (US 2017-0035969 A1) filed Sep. 30, 2016 (Feb. 9, 2017).
U.S. Appl. No. 14/076,109 (US 2014-0066890 A1) filed Nov. 8, 2013 (Mar. 6, 2014).
U.S. Appl. No. 12/785,144 (U.S. Pat. No. 8,597,274) filed May 21, 2010 (Dec. 3, 2013).
U.S. Appl. No. 16/560,497, filed Nov. 23, 2021 Issue Fee Payment.
U.S. Appl. No. 16/560,497, filed Aug. 25, 2021 Notice of Allowance.
U.S. Appl. No. 16/560,497, filed Aug. 10, 2021 Response to Final Office Action and Request for Continued Examination (RCE).
U.S. Appl. No. 16/560,497, filed May 10, 2021 Final Office Action.
U.S. Appl. No. 16/560,497, filed Mar. 17, 2021 Response to Non-Final Office Action.
U.S. Appl. No. 16/560,497, filed Nov. 23, 2020 Non-Final Office Action.
U.S. Appl. No. 15/282,688, filed Oct. 10, 2019 Abandonment.

(56) References Cited

OTHER PUBLICATIONS

U.S. Appl. No. 15/282,688, filed Apr. 4, 2019 Non-Final Office Action.
U.S. Appl. No. 14/076,109, filed Dec. 15, 2016 Abandonment.
U.S. Appl. No. 14/076,109, filed Jun. 2, 2016 Non-Final Office Action.
U.S. Appl. No. 14/076,109, filed Apr. 22, 2016 Response to Final Office Action and Request for Continued Examination (RCE).
U.S. Appl. No. 14/076,109, filed Jan. 22, 2016 Final Office Action.
U.S. Appl. No. 14/076,109, filed Nov. 9, 2015 Response to Non-Final Office Action.
U.S. Appl. No. 14/076,109, filed Jun. 11, 2015 Non-Final Office Action.
U.S. Appl. No. 14/076,109, filed May 26, 2015 Response to Restriction Requirement.
U.S. Appl. No. 14/076,109, filed Mar. 24, 2015 Restriction Requirement.
U.S. Appl. No. 12/785,144, filed Oct. 29, 2013 Issue Fee Payment.
U.S. Appl. No. 12/785,144, filed Sep. 3, 2013 Notice of Allowance.
U.S. Appl. No. 12/785,144, filed Jun. 26, 2013 Response to Non-Final Office Action.
U.S. Appl. No. 12/785,144, filed Mar. 27, 2013 Non-Final Office Action.
U.S. Appl. No. 12/785,144, filed Mar. 18, 2013 Response to Restriction Requirement.
U.S. Appl. No. 12/785,144, filed Jan. 18, 2013 Restriction Requirement.
"convolution," Wikipedia, retrieved on May 28, 2016, retrieved from: https://en.wikipedia.org/wiki/Convolution, pp. 1-14.
U.S. Appl. No. 61/246,630, filed Sep. 29, 2009.
"Getting Started with Carelink™ Personal Software For Continuous Glucose Monitoring", User Guide, Medtronic Diabetes, 28 pages (2009).
"In Vivo Glucose Sensing", Chemical Analysis, A Series of Monographs on Analytical Chemistry and its Applications, vol. 174, 466 pages (2010).
"PMA Approvals" retrieved from "https://www.fda.gov/medical-devices/device-approvals-denials-and-clearances/pma-approvals#monthly" on Sep. 14, 2022, 3 pages.
"Premarket Approval (PMA)" retrieved from "https://www.accessdata.fda.gov/scripts/cdrh/cfdocs/cfpma/pma.cfm?ID=P050020" on Sep. 14, 2022, 6 pages.
FreeStyle Navigator Continuous Glucose Monitoring System, User Guide, Abbott Diabetes Care Inc., 195 pages (2008).
Sandham, et al., "Blood Glucose Prediction for Diabetes Therapy Using a Recurrent Artificial Neural Network", 9th European Signal Processing Conference (EUSIPCO 1998), 4 pages (1998).
Sparacino, et al., "Glucose concentration can be predicted ahead in time from continuous glucose monitoring sensor time-series", IEEE Transactions on Biomedical Engineering, 54(5):931-937 (2007).
U.S. Appl. No. 17/941,586, filed Feb. 28, 2023 Notice of Allowance.
"DexCom's 7-Day STS Continuous Glucose Monitoring System", Jun. 1, 2007 https://newatlas.com/dexcoms-7-day-sts-continuous-glucose-monitoring-system/7376/ 1 page.
About Dexcom—Continuous Glucose Monitoring Company, 12 pages (2021).
Alva, S., et al., Accuracy of a 14-Day Factory-Calibrated Continuous Glucose Monitoring System With Advanced Algorithm in Pediatric and Adult Population With Diabetes, Journal of Diabetes Science and Technology, vol. 16(I), pp. 70-77 (2022).
Campbell, F. M., et al., Outcomes of using flash glucose monitoring technology by children and young people with type 1 diabetes in a single arm study, Pediatric Diabetes, pp. 1294-1301 (2018).
Deshmukh, H., et al., Effect of Flash Glucose Monitoring on Glycemic Control, Hypoglycemia, Diabetes-Related Distress, and Resource Utilization in the Association of British Clinical Diabetologists (ABCD) Nationwide Audit, Diabetes Care, 8 pages (2020).
General report of the German Diabetes Society on the state of diabetic patients and treatment methods for the year 2021, 15 pages (with English summary).
Haak, T., et al., Use of Flash Glucose-Sensing Technology for 12 months as a Replacement for Blood Glucose Monitoring in Insulin-treated Type 2 Diabetes, Diabetes Ther, 14 pages (2017).
Letter from Department of Health & Human Services, Food and Drug Administration, to Andy Balo, DexCom, Inc. re. P050012/S001, STS-7 Continuous Glucose Monitoring System dated May 31, 2007, 95 pages.
Roussel, R., et al., Important Drop in Rate of Acute Diabetes Complications in People With Type 1 or Type 2 Diabetes After Initiation of Flash Glucose Monitoring in France: The Relief Study, 5 pages, American Diabetes Association, Diabetes Care (2021).
STS®—Seven Continuous Glucose Monitoring System User's Guide, 74 pages (2007).
Summary of Safety and Effectiveness Data, STS®—7 Continuous Glucose Monitoring System, DexCom, Inc., Date of Approval: May 31, 2007, 14 pages.
Approval letter from Department of Health and Human Services re. P050012/S001, STS-7 Continuous Glucose Monitoring System, dated May 31, 2007, 7 pages.
Declaration of Thomas Foster for Taylor Wessing LLP, Hill House, 1 Little New St. London EC4A3TR ("Taylor Wessing"), signed on Jan. 30, 2024 (160 pages).
PMA Final Decisions Rendered for May 2007, The Wayback Machine, U.S. Food and Drug Administration, 21 pages.
Premarket Approval (PMA) on Seven Plus Continuous Glucose Monitoring System, Notice date: Jun. 28, 2007, 3 pages.
STS-7 Continuous Glucose Monitoring System—P050012/S001, Approved May 31, 2007, The Wayback Machine, U.S. Food and Drug Administration, 1 page.
Choudhary, et al., Insulin Pump Therapy With Automated Insulin Suspension in Response to Hypoglycemia, Reduction in nocturnal hypoglycemia in those at greatest risk, Diabetes Care, vol. 34, pp. 2023-2025 (2011).
Congress.gov, About the Congressional Record, Feb. 22, 2022, 3 pages.
Declaration of Thomas Edward Foster of Taylor Wessing LLP, Hill House, 1 Little New St. London EC4A 3TR ("Taylor Wessing"), signed on Jan. 30, 2024, 160 pages.
FDA Premarket Approval (PMA) for Seven Plus Continuous Glucose Monitoring System, Notice Date: Jun. 28, 2007, 3 pages.
Federal Register, vol. 76, No. 120, Jun. 22, 2011, pp. 36542-36543.
Hon, Urging FDA to Act Promptly to Approve Artificial Pancreas Technologies, Congressional Record (Bound Edition), vol. 157 (2011), Part 13, 3 pages.
Kowalski, Can We Really Close the Loop and How Soon? Accelerating the Availability of an Artificial Pancreas: A Roadmap to Better Diabetes Outcomes, Diabetes Technology & Therapeutics, vol. 11, pp. S-113-S-119 (2009).
Letter from Department of Health & Human Services to Mr. Andy Balo, Dexcom, Inc. re. P050012/S001, STS-7 Continuous Glucose Monitoring System, dated May 31, 2007, 7 pages.
Pickup, et al., Semi-Closed-Loop Insulin Delivery Systems: Early Experience with Low-Glucose Insulin Suspend Pumps, Diabetes Technology & Therapeutics, vol. 13, No. 7, pp. 695-698 (2011).
PMA Final Decisions Rendered for May 2007, FDA U.S. Food and Drug Administration, 21 pages.
STS-7 Continuous Glucose Monitoring System—P050012/S001, Approved May 31, 2007, FDA U.S. Food and Drug Administration, 1 page.

* cited by examiner

CONTINUOUS GLUCOSE MONITORING SYSTEM

CROSS-REFERENCE TO RELATED APPLICATIONS

The present application is a continuation of U.S. patent application Ser. No. 16/560,497, filed Sep. 4, 2019, which is a continuation of Ser. No. 15/282,688 filed on Sep. 30, 2016, which is a divisional of U.S. patent application Ser. No. 14/076,109, filed Nov. 8, 2013, which is a continuation of U.S. patent application Ser. No. 12/785,144, filed May 21, 2010, now U.S. Pat. No. 8,597,274, which claims the benefit of U.S. Provisional Appl. No. 61/180,649, filed May 22, 2009, all of which are incorporated herein by reference in their entireties for all purposes.

This application is also related to U.S. application Ser. No. 12/784,981, filed May 21, 2010, entitled "Methods For Reducing False Hypoglycemia Alarm Occurrence," and now U.S. Pat. No. 9,579,456 (U.S. Provisional No. 61/180,700, filed May 22, 2009); U.S. application Ser. No. 12/785,104, filed May 21, 2010, now U.S. Pat. No. 8,257,300, issued Sep. 4, 2012, entitled "Safety Features For Integrated Insulin Delivery System," (U.S. Provisional Application No. 61/180,627, filed May 22, 2009); U.S. application Ser. No. 12/785,096, filed May 21, 2010, now U.S. Pat. No. 8,398,616, issued May 19, 2013, entitled "Safety Layer For Integrated Insulin Delivery System," (U.S. Provisional Application No. 61/180,774, filed May 22, 2009); and U.S. application Ser. No. 12/785,196, filed May 21, 2010, entitled "Adaptive Insulin Delivery System," (U.S. Provisional Application No. 61/180,767, filed May 22, 2009).

BACKGROUND

Diabetes is a metabolic disorder that afflicts tens of millions of people throughout the world. Diabetes results from the inability of the body to properly utilize and metabolize carbohydrates, particularly glucose. Normally, the finely tuned balance between glucose in the blood and glucose in bodily tissue cells is maintained by insulin, a hormone produced by the pancreas which controls, among other things, the transfer of glucose from blood into body tissue cells. Upsetting this balance causes many complications and pathologies including heart disease, coronary and peripheral artery sclerosis, peripheral neuropathies, retinal damage, cataracts, hypertension, coma, and death from hypoglycemic shock.

In persons with insulin-dependent diabetes, the symptoms of the disease can be controlled by administering additional insulin (or other agents that have similar effects) by injection or by external or implantable insulin pumps. The "correct" insulin dosage is a function of the level of glucose in the blood. Ideally, insulin administration should be continuously readjusted in response to changes in glucose level.

Presently, systems are available for continuously monitoring a person's glucose levels by implanting a glucose sensitive probe into the person. Such probes measure various properties of blood or other tissues, including optical absorption, electrochemical potential and enzymatic products. The output of such sensors can be communicated to a hand held device or controller that is used to calculate an appropriate dosage of insulin to be delivered to the user of the continuous glucose monitor (CGM) in view of several factors, such as the user's present glucose level, insulin usage rate, carbohydrates consumed or to be consumed and exercise, among others. These calculations can then be used to control a pump that delivers the insulin, either at a controlled "basal" rate, or as a "bolus" into the user. When provided as an integrated system, the continuous glucose monitor, controller and pump work together to provide continuous glucose monitoring and insulin pump control.

Such systems can be closed loop systems, where the amount of insulin being delivered is completely controlled by the controller and pump in conjunction with glucose level data received from the CGM device. Alternatively, such systems may be open loop systems, where the user evaluates the glucose level information from a glucose monitoring device and then instructs the pump accordingly, or the system may be a semi-closed loop system that combines various aspects of a closed loop and open loop system.

Typically, present systems may be considered to be open or semi-closed loop in that they require intervention by a user to calculate and control the amount of insulin to be delivered. However, there may be periods when the user is not able to adjust insulin delivery. For example, when the user is sleeping, he or she cannot intervene in the delivery of insulin, yet control of a patient's glucose level is still necessary. A system capable of integrating and automating the functions of glucose monitoring and controlled insulin delivery into a closed loop system would be useful in assisting users in maintaining their glucose levels, especially during periods of the day when they are unable or unwilling to the required calculations to adjust insulin deliver to control their glucose level.

What has been needed, and heretofore unavailable, is an integrated, automated system combining continuous glucose monitoring and controlled insulin delivery. Such a system would include various features to insure the accuracy of the glucose monitor and to protect the user from either under- or over-dosage of insulin. The system would include various functions for improving the usability, control, and safety of the system, including a variety of alarms which could be set by a user or a technician to avoid false alarms while ensuring adequate sensitivity to protect the user. The present invention satisfies these and other needs.

SUMMARY OF THE INVENTION

Briefly, and in general terms, the invention is directed to new and improved systems and methods for management of a user's glucose level, including systems and methods for improving the usability and safety of such systems including continuous glucose monitors and a drug delivery pumps.

In one aspect, the invention is directed to a system and method for use when insulin delivery is to be restarted after an unexpected stop in delivery. In this aspect of the invention, insulin history and glucose level history are used for calculating and recommending a bolus volume of insulin to be delivered to bring a user's insulin on board, that is, residual insulin that is unmetabolised and circulating in the user's blood stream since insulin was last added, up to the level it would have been had insulin delivery not been stopped.

In another aspect, a safe amount and duration of basal rate insulin delivery is determined using model-based calculation of insulin on board, past insulin delivery information, past and present glucose information of the user and a predicted glucose profile over a near-future time horizon, among other factors, in the event that a closed loop insulin delivery system terminates closed loop operation unexpectedly.

In still another aspect, the invention includes a system and method for enhancing alarm avoidance with pre-emptive pump control command modification, which is advantageous when compared with simply muting an alarm, and is less annoying than a persistent projected low glucose alarm. In yet another aspect, a user interface is provided that integrates and cooperates with the enhanced alarm avoidance system and method to facilitate use of the system.

In a further aspect, a system and method is included that is directed to reducing the frequency of false low glucose alarms, particularly when an insulin delivery system is operating in a closed loop mode, by allowing for the possibility of the complete or partial recovery from an artifact, such as a sensor drop out, to occur prior to an alarm presentation to a user of the system. [0014] In another aspect, a model-based calculation of the present and near-future values of best estimate and upper/lower bounds of glucose is made to adjust a tiered alarm mechanism in order to account for predicted hypoglycemic and hyperglycemic events.

In yet another aspect, the invention includes a method for determining a bolus volume to be administered to make up for a cessation of basal delivery of insulin, comprising: determining an amount of insulin remaining in a user's body such that insulin remaining=amount of insulin delivered before cessation×(user's insulin action time minus the time since insulin was last delivered)/(user's insulin action time); and calculating a bolus delivery to equal the amount of basal delivery lost. In another aspect, determining an amount of insulin remaining includes using a model to estimate the amount of insulin remaining.

In still another aspect, the invention includes a method of determining an insulin delivery rate when a closed loop insulin delivery system terminates unexpectedly, comprising: a) providing a glucose level and predicting a future glucose level in order to determine the appropriate insulin bolus for the latest control action, and assuming that this commanded is immediately followed by open loop control where the pre-programmed basal delivery amount will be in effect thereafter; b) analyzing the future glucose level using this latest bolus value plus a future basal rate to determine if the future glucose level is acceptable, and if so, waiting for a selected period of time and repeating a); c) if the glucose level of b) is not acceptable, computing an alternate maximum temporary basal delivery amount that is lower than the previously assumed basal rate, such that the predicted future glucose level is acceptable, and if so, providing a temporary basal command at the computed basal rate and duration, and predicting a future glucose level; and if so, waiting for a selected period of time and repeating a); d) if the predicted future glucose level is unacceptable, projecting a future glucose level using the lowest temporary basal delivery rate computable in step c) and a maximum duration that is shorter than the maximum delivery duration, and, if the future glucose level is acceptable, providing a temporary basal command including the rate and duration of along with a nominal bolus command and then wait for a selected period of time and repeat a); and f) reducing the bolus command by minimum bolus resolution and repeat step a) such that the combination of the reduced bolus and a suitable temporary basal rate results in an acceptable predicted glucose profile if calculating a lower alternate temporary basal rate or a lower and shorter temporary basal rate does not result in an acceptable future glucose level. In still another aspect, the method further comprises alerting the user to take action to counter the effect of excessive insulin if an acceptable glucose profile cannot be obtained in step f) above.

In another aspect, the present invention includes a method for predicting insulin needs at a future time to avoid unwanted out of range alarms and adjusting current insulin delivery; comprising: providing a current glucose level; providing a future time when a predicted glucose level is required; determining the predicted level at the future time based upon the current glucose level, a value for insulin on board, current bolus parameters and current parameters defining an acceptable range of glucose levels; and adjusting insulin delivery to maintain the glucose level in a target range.

In yet another aspect, the present invention includes a method for reducing false hypoglycemic alarms in a system under closed loop control; comprising: a) providing a current glucose level; b) determining if the first level is below a threshold level and if so, providing a further glucose level at the expiration of a selected period of time; c) determining if the glucose level taken after the expiration of the selected period of time is below the threshold level, and if so, alerting the user of a low glucose condition if the time between providing the two glucose levels is greater than a selected duration of time, and if not, repeating c) until either the time since the current glucose level and the last further glucose level exceeds the selected duration of time or the last further glucose level is above the threshold level.

In yet another aspect, the present invention includes a method of adjusting glucose level alarm thresholds and alarm enunciation delay times in a system using CGM and insulin delivery system information, comprising using a model based state estimation, determining a predicted future glucose level and alerting a user only if the predicted future glucose level falls outside of a predetermined acceptable range. In an alternative aspect, the model based state estimation is a Kalman filter. In still another alternative aspect, the model based state estimation assesses the likelihood that a CGM measurement that exceeds a high or low threshold is due to a true event. In yet another alternative aspect, the model based state estimation assesses the likelihood that a CGM measurement that exceeds a high or low threshold is due to a sensor artifact.

In still another aspect, the likelihood is determined by comparing the difference between the latest CGM measurement and interstitial glucose computed by the model prior to the latest CGM measurement; and in a further aspect, the method comprises adjusting the glucose alarm enunciation by adjusting the threshold level and duration in which the CGM measurement exceeds a given threshold before an alarm is enunciated.

In yet another aspect, where a decreasing CGM signal close to a low threshold alarm value that is not accompanied by a corresponding amount of insulin history will result in a low threshold alarm being made less sensitive by lowering the threshold value and/or increasing the duration of delay before the CGM signal results in enunciation of a low threshold alarm. In an alternative aspect, where a decreasing CGM signal close to a low threshold alarm value that is accompanied by an insulin history that should have generated a much lower CGM value than is measured results in a low threshold alarm being made more sensitive by increasing the threshold value and/or decreasing the duration of delay before the CGM signal results in the enunciation of a low threshold alarm. In still another alternative aspect, where an increasing CGM signal close to a high threshold alarm value that is not accompanied by an appreciable amount of insulin history results in a high threshold alarm being made more sensitive by lowering the threshold value and/or decreasing the duration of delay before the CGM signal results in the enunciation of a high threshold alarm. In yet another alternative aspect, where an increasing CGM signal close to a high threshold alarm value that is accompanied by an appreciable amount of insulin history results in a high threshold alarm being made less sensitive by increasing the threshold value and/or increasing the duration of delay before the CGM signal results in the enunciation of a high threshold alarm.

In another aspect, the present invention a method of determining a latest insulin delivery amount and a temporary insulin delivery rate to be delivered when a closed loop insulin delivery system terminates unexpectedly, comprising a) providing a glucose level and predicting a future glucose level in order to determine the appropriate insulin amount for the latest control action, and assuming that this commanded is immediately followed by open loop control where the preprogrammed temporary basal rate will be in effect thereafter; b) analyzing the future glucose level using this latest insulin amount plus a future temporary basal rate to determine if the future glucose level is acceptable, and if so, waiting for a selected period of time and repeating a); c) if the glucose level of b) is not acceptable, computing an alternate maximum temporary basal delivery amount that is lower than the previously assumed basal rate, such that the predicted future glucose level is acceptable, and if so, providing a temporary basal command at the computed basal rate and duration, and predicting a future glucose level; and if so, waiting for a selected period of time and repeating a); d) if the predicted future glucose level is unacceptable, projecting a future glucose level using the lowest temporary basal delivery rate computable in c) and a maximum duration that is shorter than the maximum delivery duration, and, if the future glucose level is acceptable, providing a temporary basal command including the rate and duration of along with a nominal latest insulin delivery command and then wait for a selected period of time and repeat a); and f) reducing the latest insulin delivery command by a predetermined minimum insulin delivery resolution and repeat a) such that the combination of the reduced latest insulin delivery amount and a suitable temporary basal rate results in an acceptable predicted glucose profile if calculating a lower alternate temporary basal rate or a lower and shorter temporary basal rate does not result in an acceptable future glucose level.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

For the purposes of promoting an understanding of the principles of the invention, reference will now be made to a number of illustrative embodiments shown in the attached drawings and specific language will be used to describe the same. It will be understood that throughout this document, the terms "user" and "patient" are used interchangeably.

Figure 1:
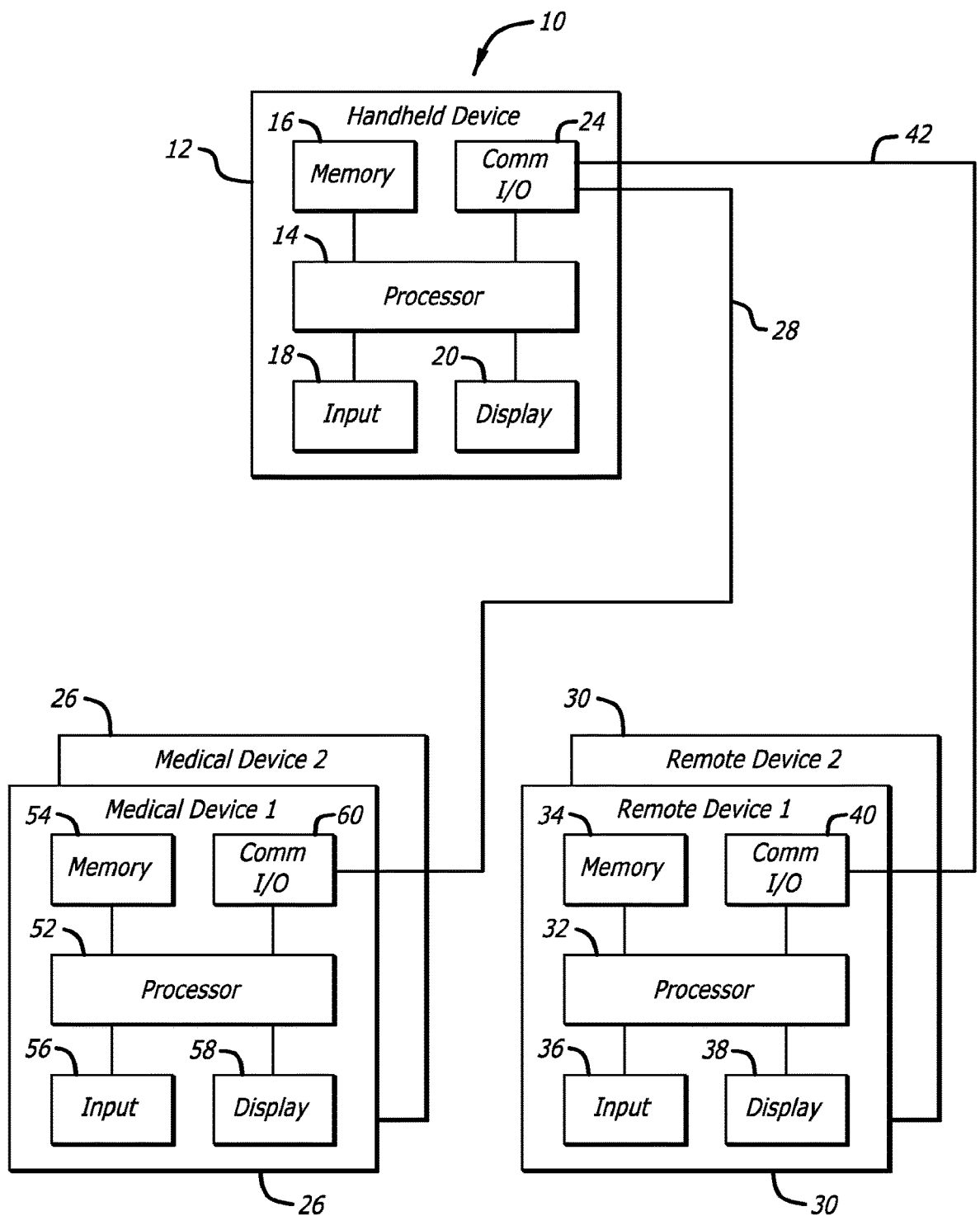
FIG. 1 is a schematic diagram illustrating an exemplary embodiment of a controller and its various components in operable communication with one or more medical devices, such as a glucose monitor or drug delivery pump, and optionally, in operable communication with a remote controller device.

Referring now to FIG. 1, a block diagram of one illustrative embodiment of a system 10 for determining drug administration information is shown. In the illustrated embodiment, the system 10 includes an electronic device 12, which may be handheld, having a processor 14 in data communication with a memory unit 16, an input device 18, a display 20, and a communication input/output unit 24. The electronic device 12 may be provided in the form of a general purpose computer, central server, personal computer (PC), lap top or notebook computer, personal data assistant (PDA), programmable telephone or cellular phone or other hand-held device, external infusion pump, glucose meter, analyte sensing system, or the like. The electronic device 12 may be configured to operate in accordance with one or more conventional operating systems including for example, but not limited to, the Windows® operating system (distributed by Microsoft Corporation), the Linux operating system, the Mac OS® (distributed by Apple, Inc.) and embedded operating systems such as the QNX® operating system (distributed by QNX Software Systems), the eCOS® operating system (distributed by eCosCentric Limited), Windows CE® (distributed by Microsoft Corporation) and the Palm® operating system (distributed by Palm Inc.), and may be configured to process data according to one or more conventional internet protocols for example, but not limited to, NetBios, TCP/IP and AppleTalk® (Apple, Inc.). In any case, the electronic device 12 forms part of a fully closed-loop, semi closed-loop, or open loop diabetes control system.

The processor 14 is microprocessor-based, although processor 14 may alternatively be formed of one or more general purpose and/or application specific circuits and operable as described hereinafter. The processor 14 is programmed using appropriate software commands that may be stored in the memory or communicated to the processor 14 as needed. The memory unit 16 includes sufficient capacity to store data, one or more software algorithms executable by the processor 14 and other data. The memory unit 16 may include one or more conventional memory or other data storage devices. Electronic device 12 may also include an integrated glucose meter for use in calibrating a continuous glucose monitor (CGM) or for calculating insulin amounts for bolus delivery.

The input device 18 may be used in a conventional manner to input and/or modify data. The display 20 is also included for viewing information relating to operation of the device 12 and/or system 10. Such a display may be a conventional display device including for example, but not limited to, a light emitting diode (LED) display, a liquid crystal display (LCD), a cathode ray tube (CRT) display, or the like. Alternatively or additionally, the display 20 may be or include an audible display configured to communicate information to a user, another person, or another electronic system having audio recognition capabilities via one or more coded patterns, vibrations, synthesized voice responses, or the like. Alternatively or additionally, the display 20 may be or include one or more tactile indicators configured to display or annunciate tactile information that may be discerned by the user or another person.

The input device 18 may be or include a conventional keyboard or keypad for entering alphanumeric data into the processor 14. Such a keyboard or keypad may include one or more keys or buttons configured with one or more tactile indicators to allow users with poor eyesight to find and select an appropriate one or more of the keys, and/or to allow users to find and select an appropriate one or more of the keys in poor lighting conditions. Alternatively or additionally, the input device 18 may be or include a conventional mouse or other conventional point and click device for selecting information presented on the display 20. Alternatively or additionally, the input device 18 may include the display 20 configured as a graphical user interface (GUI). In this embodiment, the display 20 may include one or more selectable inputs that a user may select by touching an appropriate portion of the display 20 using an appropriate implement. Alternatively, the display 20 may be configured as a touch-screen capable of responding to user activation to, for example, enter data or select device functions.

Alternatively, the input device 18 may also include a number of switches or buttons that may be activated by a user to select corresponding operational features of the device 12 and/or system 10. Input device 18 may also be or include voice-activated circuitry responsive to voice commands to provide corresponding input data to the processor 14. In any case, the input device 18 and/or display 20 may be included with or separate from the electronic device 12.

System 10 may also include a number of medical devices which carry out various functions, for example, but not limited to, monitoring, sensing, diagnostic, communication and treatment functions. In such embodiments, any of the one or more of the medical devices may be implanted within the user's body, coupled externally to the user's body (e.g., such as an infusion pump), or separate from the user's body. Alternatively or additionally, one or more of the medical devices may be mounted to and/or form part of the electronic device 12. Typically, the medical devices are each configured to communicate wirelessly with the communication I/O unit 24 of the electronic device 12 via one of a corresponding number of wireless communication links.

The wireless communications between the various components of the system 10 may be one-way or two-way. The form of wireless communication used may include, but is not limited to, radio frequency (RF) communication, infrared (IR) communication, Wi-Fi, RFID (inductive coupling) communication, acoustic communication, capacitive signaling (through a conductive body), galvanic signaling (through a conductive body), or the like. In any such case, the electronic device 12 and each of the medical devices include conventional circuitry for conducting such wireless communications circuit. Alternatively, one or more of the medical devices may be configured to communicate with the electronic device 12 via one or more conventional serial or parallel configured hardwire connections therebetween.

Each of the one or more medical devices 26 may include one or more of a conventional processing unit 52, conventional input/output circuitry and/or devices 56, 58 communication ports 60 and one or more suitable data and/or program storage devices 58. It will be understood that not all medical devices 26 will have the same componentry, but rather will only have the components necessary to carry out the designed function of the medical device. For example, in one embodiment, a medical device 26 may be capable of integration with electronic device 12 and remote device 30. In another embodiment, medical device may also be capable of standalone operation, should communication with electronic device 12 or remote device 30 be interrupted. In another embodiment, medical device 26 may include processor, memory and communication capability, but does not have a display 58 or input 56. In still another embodiment, the medical device 26 may include an input 56, but lack a display 58.

In some embodiments, the system 10 may alternatively or additionally include a remote device 30. The remote device 30 may include a processor 32, which may be identical or similar to the processor 14, a memory or other data storage unit 34, an input device 36, which may be or include any one or more of the input devices described hereinabove with respect to the input device 18, a display unit 38, which may be or include any one or more of the display units described hereinabove with respect to the display unit 20, and communication I/O circuitry 40. The remote device 30 may be configured to communicate with the electronic device 12 or medical devices(s) 26 via any wired or wireless communication interface 42, which may be or include any of the communication interfaces or links described hereinabove. Although not shown, remote device 30 may also be configured to communicate directly with one or more medical devices 26, instead of communicating with the medical device 26 through electronic device 12.

The system 10 illustrated in FIG. 1 is, or forms part of, a fully closed-loop, semi closed-loop, or open loop diabetes control arrangement. In this regard, the system 10 requires user input of some amount of information from which the system 10 determines, at least in part, insulin bolus administration information. Such insulin bolus administration information may be or include, for example, insulin bolus quantity or quantities, bolus type, insulin bolus delivery time, times or intervals (e.g., single delivery, multiple discrete deliveries, continuous delivery, etc.), and the like. Examples of user supplied information may be, for example but not limited to, user glucose concentration, interstitial glucose level information, information relating to a meal or snack that has been ingested, is being ingested, or is to be ingested sometime in the future, user exercise information, user stress information, user illness information, information relating to the user's menstrual cycle, and the like. In any case, the system 10 includes a delivery mechanism for delivering controlled amounts of a drug; such as, for example, insulin, glucagon, incretin, or the like, and/or offering an alternatively actionable therapy recommendation to the user via the display 20, such as, for example, directions or instructions related to ingesting carbohydrates, exercising, and the like.

The system 10 may be provided in any of a variety of configurations, and examples of some such configurations will now be described. It will be understood, however, that the following examples are provided merely for illustrative purposes, and should not be considered limiting in any way. Those skilled in the art may recognize other possible implementations of a fully closed-loop, semi closed-loop, or open loop diabetes control arrangement, and any such other implementations are contemplated by this disclosure.

In a first exemplary implementation of the system 10, the electronic device 12 is provided in the form of an insulin pump configured to be worn externally to the user's body and also configured to controllably deliver insulin to the user's body. In this example, the medical devices 26 may include one or more implanted sensors and/or sensor techniques for providing information relating to the physiological condition of the user. Examples of such implanted sensors may include, but should not be limited to, a glucose sensor, a body temperature sensor, a blood pressure sensor, a heart rate sensor, one or more bio-markers configured to capture one or more physiological states of the body, such as, for example, HBA1C, or the like.

In implementations that include an implanted glucose sensor, the system 10 may be a fully closed-loop system operable in a conventional manner to automatically monitor glucose and deliver insulin, as appropriate, to maintain glucose at desired levels. The various medical devices may alternatively or additionally include one or more sensors or sensing systems that are external to the user's body and/or sensor techniques for providing information relating to the physiological condition of the user. Examples of such sensors or sensing systems may include, but should not be limited to, a glucose strip sensor/meter, a body temperature sensor, a blood pressure sensor, a heart rate sensor, one or more bio-markers configured to capture one or more physiological states of the body, such as, for example, HBA1C, or the like.

In implementations that include an external glucose sensor, the system 10 may be a closed-loop, semi closed-loop, or open loop system operable in a conventional manner to deliver insulin, as appropriate, based on glucose information provided thereto by the user. Information provided by any such sensors and/or sensor techniques may be communicated to the system 10 using any one or more conventional wired or wireless communication techniques. In this exemplary implementation, the remote device 30 may also be included in the form of a handheld or otherwise portable electronic device configured to communicate information to and/or from the electronic device 12.

In a second exemplary implementation of the system 10, the electronic device 12 is provided in the form of a handheld remote device, such as a PDA, programmable cellular phone, or other handheld device. In this example, the medical devices 26 include at least one conventional implantable or externally worn drug pump. In one embodiment of this example, an insulin pump is configured to controllably deliver insulin to the user's body. In this embodiment, the insulin pump is configured to wirelessly transmit information relating to insulin delivery to the handheld device 12. The handheld device 12 is configured to monitor insulin delivery by the pump, and may further be configured to determine and recommend insulin bolus amounts, carbohydrate intake, exercise, and the like. The system 10 may or may not be configured in this embodiment to provide for transmission of wireless information from the handheld device 12 to the insulin pump.

In an alternate embodiment of this example, the handheld device 12 is configured to control insulin delivery to the user by determining insulin delivery commands and transmitting such commands to the insulin pump. The insulin pump, in turn, is configured to receive the insulin delivery commands from the handheld device 12, and to deliver insulin to the user according to the commands. The insulin pump, in this embodiment, may or may not further process the insulin pump commands provided by the handheld unit 12. In any case, the system 10 will typically be configured in this embodiment to provide for transmission of wireless information from the insulin pump back to the handheld device 12 to thereby allow for monitoring of pump operation. In either embodiment of this example, the system 10 may further include one or more implanted and/or external sensors of the type described in the previous example. In this exemplary implementation, a remote device 30 may also be included in the form of, for example, a PC, PDA, programmable cellular phone, laptop or notebook computer configured to communicate information to and/or from the electronic device 12.

Those skilled in the art will recognize other possible implementations of a fully closed-loop, semi closed-loop, or open loop diabetes control arrangement using at least some of the components of the system 10 illustrated in FIG. 1. For example, the electronic device 12 in one or more of the above examples may be provided in the form of a PDA, programmable cellular phone, laptop, notebook or personal computer configured to communicate with one or more of the medical devices 26, at least one of which is an insulin delivery system, to monitor and/or control the delivery of insulin to the user. As another example, the remote device 30 may be configured to communicate with the electronic device 12 and/or one or more of the medical devices 26, to control and/or monitor insulin delivery to the patient, and/or to transfer one or more software programs and/or data to the electronic device 12. The remote device 30 may reside in a caregiver's office or other remote location, and communication between the remote device and any component of the system 10 may be accomplished via an intranet, internet (such as, for example, through the world-wide-web), cellular, telephone modem, RF, or other communication link. Any one or more conventional internet protocols may be used in such communications. Alternatively or additionally, any conventional mobile content delivery system; such as, for example, Wi-Fi, WiMAX, short message system (SMS), or other conventional message scheme may be used to provide for communication between devices comprising the system 10.

Generally, the concentration of glucose in a person changes as a result of one or more external influences such as meals and exercise, and also changes resulting from various physiological mechanisms such as stress, illness, menstrual cycle and the like. In a person with diabetes, such changes can necessitate monitoring the person's glucose level and administering insulin or other glucose level altering drug, such as, for example, a glucose lowering or raising drug, as needed to maintain the person's glucose level within a desired range. In any of the above examples, the system 10 is thus configured to determine, based on some amount of patient-specific information, an appropriate amount, type and/or timing of insulin or other glucose level altering drug to administer in order to maintain normal glucose levels without causing hypoglycemia or hyperglycemia. In some embodiments, the system 10 is configured to control one or more external insulin pumps, such as, for example, subcutaneous, transcutaneous or transdermal pumps, and/or implanted insulin pumps to automatically infuse or otherwise supply the appropriate amount and type of insulin to the user's body in the form of one or more insulin boluses.

In other embodiments, the system 10 is configured to display or otherwise notify the user of the appropriate amount, type, and/or timing of insulin in the form of an insulin delivery or administration recommendation or instruction. In such embodiments, the hardware and/or software forming system 10 allows the user to accept the recommended insulin amount, type, and/or timing, or to reject it. If the recommendation is accepted by the user, the system 10, in one embodiment, automatically infuses or otherwise provides the appropriate amount and type of insulin to the user's body in the form of one or more insulin boluses. If, on the other hand, the user rejects the insulin recommendation, the hardware and/or software forming system 10 allows the user to override the system 10 and manually enter values for insulin bolus quantity, type, and/or timing in the system. The system 10 is thus configured by the user to automatically infuse or otherwise provide the user specified amount, type, and/or timing of insulin to the user's body in the form of one or more insulin boluses.

Alternatively, the appropriate amount and type of insulin corresponding to the insulin recommendation displayed by the system 10 may be manually injected into, or otherwise administered to, the user's body. It will be understood, however, that the system 10 may alternatively or additionally be configured in like manner to determine, recommend, and/or deliver other types of medication to a patient.

The system 10 is operable, as just described, to determine and either recommend or administer an appropriate amount of insulin or other glucose level lowering drug to the patient in the form of one or more insulin boluses. In order to determine appropriate amounts of insulin to be delivered or administered to the user to bring the user's glucose level within an acceptable range, the system 10 requires at least some information relating to one or more external influences and/or various physiological mechanisms associated with the user. For example, if the user is about to ingest, is ingesting, or has recently ingested, a meal or snack, the system 10 generally requires some information relating to the meal or snack to determine an appropriate amount, type and/or timing of one or more meal compensation boluses of insulin. When a person ingests food in the form of a meal or snack, the person's body reacts by absorbing glucose from the meal or snack over time. For purposes of this document, any ingesting of food may be referred to hereinafter as a "meal," and the term "meal" therefore encompasses traditional meals, such as, for example, breakfast, lunch and dinner, as well as intermediate snacks, drinks, and the like.

Figure 2:
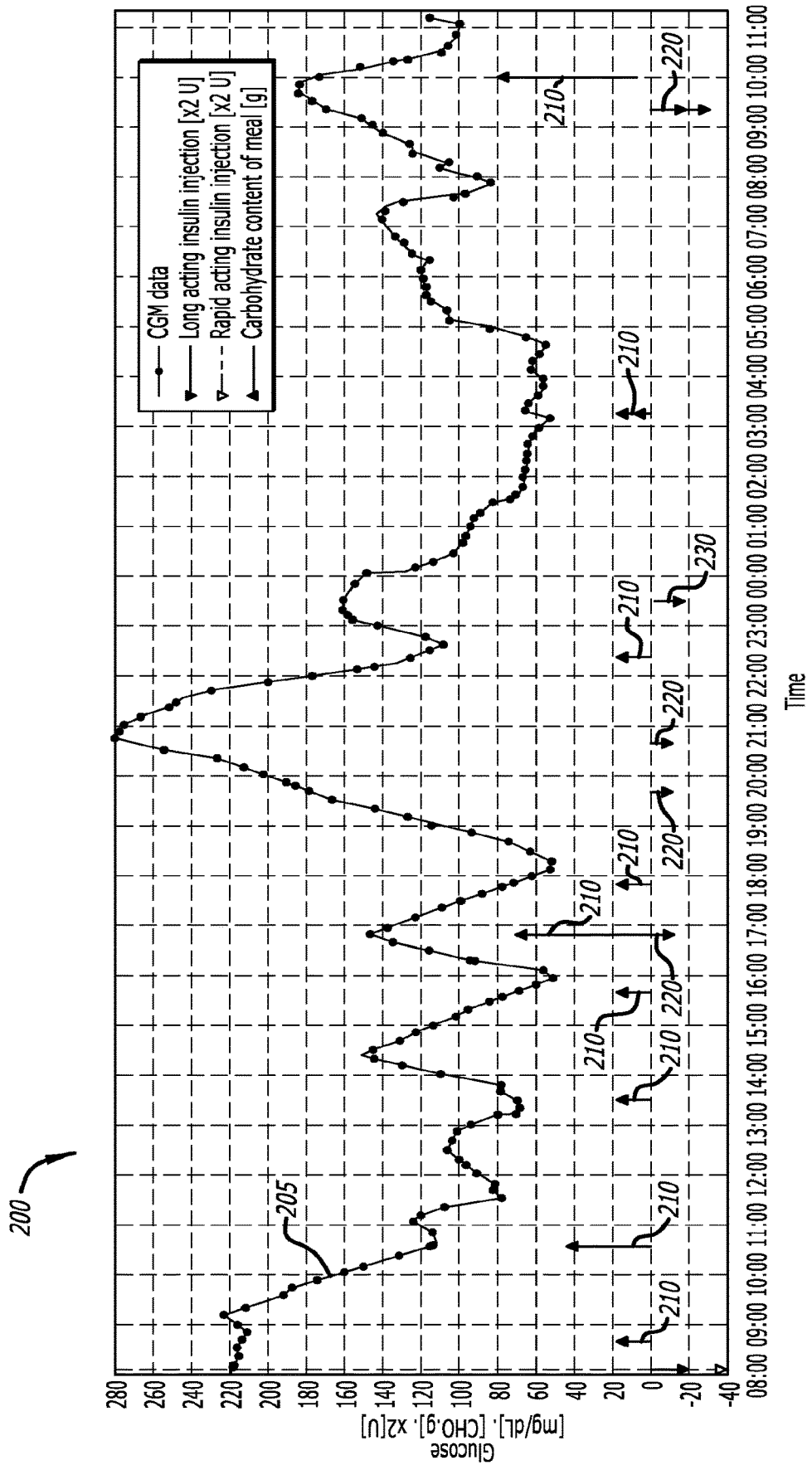
FIG. 2 is a graphical representation of a glucose profile showing glucose level measured using a CGM sensor as a function of time, and also showing the variation of the glucose level as function of carbohydrate intake and insulin administration.

FIG. 2 depicts a typical glucose absorption profile 200 for a user measured using a CGM sensor. The graph 205 plots the measured glucose level as a function of time. This profile shows the effect on glucose level of various actions, such as carbohydrate intake 210, and the delivery of rapid acting insulin 210 and long acting insulin 230.

The general shape of a glucose absorption profile for any person rises following ingestion of the meal, peaks at some measurable time following the meal, and then decreases thereafter. The speed, that is, the rate from beginning to completion, of any one glucose absorption profile typically varies for a person by meal composition, meal type or time (such as, for example, breakfast, lunch, dinner, or snack) and/or according to one or more other factors, and may also vary from day-to-day under otherwise identical meal circumstances. Generally, the information relating to such meal intake information supplied by the user to the system 10 should contain, either explicitly or implicitly, an estimate of the carbohydrate content of the meal or snack, corresponding to the amount of carbohydrates that the user is about to ingest, is ingesting, or has recently ingested, as well as an estimate of the speed of overall glucose absorption from the meal by the user.

The estimate of the amount of carbohydrates that the patient is about to ingest, is ingesting, or has recently ingested, may be provided by the user in any of various forms. Examples include, but are not limited to, a direct estimate of carbohydrate weight (such as, for example, in units of grams or other convenient weight measure), an amount of carbohydrates relative to a reference amount (such as, for example, dimensionless), an estimate of meal or snack size (such as, for example, dimensionless), and an estimate of meal or snack size relative to a reference meal or snack size (such as, for example, dimensionless). Other forms of providing for user input of carbohydrate content of a meal or snack will occur to those skilled in the art, and any such other forms are contemplated by this disclosure.

The estimate of the speed of overall glucose absorption from the meal by the user may likewise be provided by the user in any of various forms. For example, for a specified value of the expected speed of overall glucose absorption, the glucose absorption profile captures the speed of absorption of the meal taken by the user. As another example, the speed of overall glucose absorption from the meal by the user also includes time duration between ingesting of the meal by a user and the peak glucose absorption of the meal by that user, which captures the duration of the meal taken by the user. The speed of overall glucose absorption may thus be expressed in the form of meal speed or duration. Examples of the expected speed of overall glucose absorption parameter in this case may include, but are not limited to, a compound parameter corresponding to an estimate of the meal speed or duration (such as, for example, units of time), a compound parameter corresponding to meal speed or duration relative to a reference meal speed or duration (such as, for example, dimensionless), or the like.

As another example of providing the estimate of the expected speed of overall glucose absorption parameter, the shape and duration of the glucose absorption profile may be mapped to the composition of the meal. Examples of the expected speed of overall glucose absorption parameter in this case may include, but are not limited to, an estimate of fat amount, protein amount and carbohydrate amount (such as, for example, in units of grams) in conjunction with a carbohydrate content estimate in the form of meal size or relative meal size, an estimate of fat amount, protein amount and carbohydrate amount relative to reference fat, protein and carbohydrate amounts in conjunction with a carbohydrate content estimate in the form of meal size or relative meal size, and an estimate of a total glycemic index of the meal or snack (such as, for example, dimensionless), wherein the term "total glycemic index" is defined for purposes of this document as a parameter that ranks meals and snacks by the speed at which the meals or snacks cause the user's glucose level to rise. Thus, for example, a meal or snack having a low glycemic index produces a gradual rise in glucose level whereas a meal or snack having a high glycemic index produces a fast rise in glucose level. One exemplary measure of total glycemic index may be, but is not limited to, the ratio of carbohydrates absorbed from the meal and a reference value, such as, for example, derived from pure sugar or white bread, over a specified time period, such as, for example, 2 hours. Other forms of providing for user input of the expected overall speed of glucose absorption from the meal by the patient, and/or for providing for user input of the expected shape and duration of the glucose absorption profile generally will occur to those skilled in the art, and any such other forms are contemplated by this disclosure. [0054] Generally, the concentration of glucose in a person with diabetes changes as a result of one or more external influences such as meals and/or exercise, and may also change resulting from various physiological mechanisms such as stress, menstrual cycle and/or illness. In any of the above examples, the system 10 responds to the measured glucose by determining the appropriate amount of insulin to administer in order to maintain normal glucose levels without causing hypoglycemia. In some embodiments, the system 10 is implemented as a discrete system with an appropriate sampling rate, which may be periodic, aperiodic or triggered, although other continuous systems or hybrid systems may alternatively be implemented as described above. [0055] As one example of a conventional diabetes control system, one or more software algorithms may include a collection of rule sets which use (1) glucose information, (2) insulin delivery information, and/or (3) user inputs such as meal intake, exercise, stress, illness and/or other physiological properties to provide therapy, and the like, to manage the user's glucose level. The rule sets are generally based on observations and clinical practices as well as mathematical models derived through or based on analysis of physiological mechanisms obtained from clinical studies. In the exemplary system, models of insulin pharmacokinetics and pharmacodynamics, glucose pharmacodynamics, meal absorption and exercise responses of individual patients are used to determine the timing and the amount of insulin to be delivered. A learning module may be provided to allow adjustment of the model parameters when the patient's overall performance metric degrades such as, for example, adaptive algorithms, using Bayesian estimates, may be implemented. An analysis model may also be incorporated which oversees the learning to accept or reject learning. Adjustments are achieved utilizing heuristics, rules, formulae, minimization of cost function(s) or tables (such as, for example, gain scheduling).

Predictive models can be programmed into the processor(s) of the system using appropriate embedded or inputted software to predict the outcome of adding a controlled amount of insulin or other drug to a user in terms of the an expected glucose value. The structures and parameters of the models define the anticipated behavior.

Any of a variety of conventional controller design methodologies, such as PID systems, full state feedback systems with state estimators, output feedback systems, LQG (Linear-Quadratic-Gaussian) controllers, LQR (Linear-Quadratic-Regulator) controllers, eigenvalue/eigenstructure controller systems, and the like, could be used to design algorithms to perform physiological control. They typically function by using information derived from physiological measurements and/or user inputs to determine the appropriate control action to use. While the simpler forms of such controllers use fixed parameters (and therefore rules) for computing the magnitude of control action, the parameters in more sophisticated forms of such controllers may use one or more dynamic parameters. The one or more dynamic parameters could, for example, take the form of one or more continuously or discretely adjustable gain values. Specific rules for adjusting such gains could, for example, be defined either on an individual basis or on the basis of a user population, and in either case will typically be derived according to one or more mathematical models. Such gains are typically scheduled according to one or more rule sets designed to cover the expected operating ranges in which operation is typically nonlinear and variable, thereby reducing sources of error.

Model based control systems, such as those utilizing model predictive control algorithms, can be constructed as a black box wherein equations and parameters have no strict analogs in physiology. Rather, such models may instead be representations that are adequate for the purpose of physiological control. The parameters are typically determined from measurements of physiological parameters such as glucose level, insulin concentration, and the like, and from physiological inputs such as food intake, alcohol intake, insulin doses, and the like, and also from physiological states such as stress level, exercise intensity and duration, menstrual cycle phase, and the like. These models are used to estimate current glucose level or to predict future glucose levels. Such models may also take into account unused insulin remaining in the user after a bolus of insulin is given, for example, in anticipation of a meal. Such unused insulin will be variously described as unused, remaining, or "insulin on board."

Insulin therapy is derived by the system based on the model's ability to predict glucose levels for various inputs. Other conventional modeling techniques may be additionally or alternatively used to predict glucose levels, including for example, but not limited to, building models from first principles.

In a system as described above, the controller is typically programmed to provide a "basal rate" of insulin delivery or administration. Such a basal rate is the rate of continuous supply of insulin by an insulin delivery device such as a pump that is used to maintain a desired glucose level in the user. Periodically, due to various events that affect the metabolism of a user, such as eating a meal or engaging in exercise, a "bolus" delivery of insulin is required. A "bolus" is defined as a specific amount of insulin that is required to raise the blood concentration of insulin to an effective level to counteract the affects of the ingestion of carbohydrates during a meal and also takes into account the affects of exercise on the glucose level of the user.

As described above, an analyte monitor may be used to continuously monitor the glucose level of a user. The controller is programmed with appropriate software and uses models as described above to predict the effect of carbohydrate ingestion and exercise, among other factors, on the predicted level of glucose of the user at a selected time. Such a model must also take into account the amount of insulin remaining in the blood stream from a previous bolus or basal rate infusion of insulin when determining whether or not to provide a bolus of insulin to the user.

In a typical situation, an insulin pump normally delivers insulin without user intervention when delivering the insulin at the basal insulin delivery rate. At times, however, the pump may detect conditions that warrant providing an alarm or other signal to the user that intervention in the insulin delivery by the user is necessary. Depending on the conditions and the user's response, the controller may instruct the pump to stop delivering insulin.

When insulin delivery is stopped, the user will eventually need to restart insulin delivery. In view of the period of time during which insulin delivery was stopped, the user may need to deliver a correction bolus of insulin to bring their glucose level back within an acceptable range. The volume of the insulin bolus is calculated by the user from their current glucose level and their experience with managing their diabetes. For example, users who have experience in managing their diabetes are typically able to estimate the various factors that need to be considered in calculating a corrective bolus dosage of insulin.

In one example, the size of the corrective bolus required to maintain the user in euglycemia is related to the manner and duration in which delivery of insulin was stopped. For example, if insulin delivery was stopped for a few minutes, perhaps no corrective bolus of insulin is required. However, if insulin delivery is stopped for several hours, a significant bolus of insulin may be required to bring the user's glucose level into an acceptable range.

The controller of the system monitors the insulin pump and when the pump determines that the user wants to restart the pump, the pump may either confirm that the user wants to restart basal rate delivery of insulin, or it may prompt the user to administer a manual bolus of insulin.

In one embodiment of the invention, the controller and/or pump has a memory that stores information related to the history of the user's glucose levels and various actions or events that have been taken to adjust those levels, such as the rate of basal delivery of insulin, the amount of the last insulin bolus delivery, and the time between various events or user actions. The controller and/or pump may also store the time that has elapsed since the pump was stopped. Additional factors that may be considered include the user's insulin sensitivity, the amount of insulin that may remain in the user's blood stream since the last basal or bolus insulin delivery and whether or not an event or action may have incurred that would cause the basal rate of insulin delivery to have changed since the pump was stopped.

When the user desires to restart the pump, the controller and/or pump may, using the data programmed within the memory regarding the user's history of insulin delivery and glucose levels resulting therefrom, calculate a bolus volume of insulin to deliver using a model such as set forth as:

Remaining insulin=delivered volume×(IATIME−time)/IATIME,

Where:
Delivered volume is the amount of insulin delivered,
time is the time since the insulin was delivered, and
IATIME is the user's insulin action time, which is a measure of how long insulin remains active in an individual user's body.

Those skilled in the art will understand that other models can be used to perform this estimation, such as, for example, the decaying exponential model or model using an S-model decay.

For basal delivery, the times since the insulin was last delivered, or the age of the delivery, is not a constant. The calculation is a convolution of the basal profile function and the linear decay function.

In practice, basal insulin delivery is not delivered continuously, but instead is accumulated and delivered at discrete times. For example, an exemplary insulin pump may be programmed to deliver three minutes of basal rate insulin delivery spaced three minutes apart. This simplifies the above calculation to the dot product of two vectors. For example, D=vector of deliveries that were not performed, oldest to newest. For example,
D=(0.3, 0.3, 0.3, 0.3, 0.3, 0.3, 0.3, 0.3, 0.3, 0.3, 0.5, 0.5, 0.5, 0.5, 0.5, 0.5, 0.5, 0.5, 0.5, 0.5) which represents 20 deliveries of 0.3 and 0.5 units spaced three minutes apart.
Similarly, T=vector or time multipliers.
For example, if the insulin action time of the patient is 60 minutes and delivery has been stopped for 42 minutes, then:
T equals (0.00, 0.00, 0.00, 0.00, 0.00, 0.00, 0.35, 0.40, 0.45, 0.50, 0.55, 0.60, 0.65, 0.70, 0.75, 0.80, 0.85, 0.90, 0.95, 1.00).
The dot product of D*T equal 4.39 units.

Thus, for this example, the user will need to either manually administer or program the pump to administer 4.39 units of insulin, the bolus volume that will provide the same value for the insulin onboard for the user had the basal delivery of insulin not been stopped.

In another embodiment of the present invention using a closed looped control system, the controller or pump may be programmed to perform a model-based calculation of transitory insulin using an insulin bolus command as the nominal input for the model. This process provides a means to use model-based calculation of insulin onboard (JOB) past insulin delivery information, and past and present glucose information and predicted glucose profile over a near-future horizon to determine a safe amount and duration of basal rate in the event that a closed loop system that normally uses bolus insulin deliver terminates its operation unexpectedly.

[0074] Automated closed loop systems that regulate glucose levels by using insulin delivery have to account for instances when the closed loop system terminates and switches to open loop control. For users with insulin pumps, open-loop operation typically includes a pre-programmed insulin basal rate as well as a bolus insulin delivery rate administered in response to known events, such as a meal. When a system transitions from open to closed loop, past insulin delivery information is available from the memory and can be used by the closed loop controller to determine the best and safest insulin delivery profile for the user.

One hazard mitigated by this process is related to the transition from closed loop to open loop operation, such as, for example, in the case where a controller under closed loop control has determined a series of insulin commands that may require subsequent insulin deliveries to be lower than the open loop pre-programmed basal insulin delivery rate. As long as the system remains in closed loop operation, this is not an issue. However, should the system transition to open loop operation, having the pump deliver insulin at the pre-programmed basal rate could result in unwanted hypoglycemia if the controller previously ordered the pump to deliver insulin at a rate and duration that resulted in a large residual IOB with a plan to control the delivery in the future to significantly reduce the insulin delivery at a rate below the pre-programmed basal rate.

One embodiment of the invention addresses the situation where the closed loop system operates by delivering bolus insulin commands at a fixed interval in time, and the closed-loop system periodically obtains glucose measurement from a glucose measuring device. Such a system is also capable of issuing a temporary basal rate command to the pump with a specified amount and duration in which the basal command should apply since the command was issued. When the duration of such a demand expires, the system reverts to the pre-programmed basal rate.

As used in this description of the various embodiments of the invention, the latest command intended for normal operation of the system is described in terms of "bolus commands." Alternatively, the safety command intended to be used when closed loop operation of the system is interrupted is described in terms of a "temporary basal rate" command. The replacement of the normal operation command in terms of bolus with basal rate does not change the mechanism of the various embodiments of the invention. Using bolus and basal rate for the normal operation and the safety-related commands clarifies the roles of those commands in the description of the various embodiments of the invention included herein.

In another embodiment of the invention, the closed loop system is able to track the IOB amount by utilizing insulin pharmacokinetic and pharmacodynamic models, and by keeping track of insulin delivery data corresponding to the actual delivery of insulin to the user. This delivery data includes bolus and basal insulin amounts commanded by the user or by the automated closed loop controller.

For example, the model used by the controller to calculate insulin delivery rates may utilize a pharmacokinetic model, such as a modified version of a model used by Hovorka et al.:

$$\frac{\partial (i1(t))}{\partial t} = \frac{-1(t)}{\text{tau\_i}} + u(t)$$

$$\frac{\partial (i2(t))}{\partial t} = \frac{[i2(t) - i1(t)]}{tau\_i}$$

$$i(t) = \frac{i2(t)}{MCRWtau\_i}$$

Where:
(t) denotes variables and/or states that vary in time;
u(t) is the amount of insulin bolus given at any time t;
i1(t) and i2(t) are internal states of the insulin absorption;
i(t) is the plasma insulin concentration;
tau i is the time-to-peak of insulin absorption;
MCR is the metabolic clearance rate; and
W is the user's weight.

An example of an insulin pharmacodynamic model that may be programmed into the controller or pump using suitable software or hardware commands is given by:

$$\frac{\partial (x(t))}{\partial t} = -p][x()t) - i(t)]$$

$$\frac{\partial (g(t))}{\partial t} = -[Sg + [Si \cdot x(t)]]g(t) = [Sg \cdot g)(t)] + Sm \cdot \frac{\partial (gm(t))}{dt}]$$

Where:
Sg is the glucose clearance rated independent of insulin;
Si is the glucose clearance rate due to insulin;
g0(t) is a slowly varying equilibrium for the glucose clearance independent of insulin;
Sm is the glucose appearance constant due to meal absorption; and $$\frac{\partial (gm(t)}{\partial t}$$

is the rate of glucose appearance due to meal absorption.

In this model, the first equation governs the effective insulin x(t) over time as a function of plasma insulin i(t), given a decay time constant of 1/pl. The second equation governs how glucose g(t) varies over time as a function of many factors, including, for example, the insulin pharmacodynamics −Si x(t) g(t).

At any given time, the closed loop system is able to estimate the latest glucose by utilizing the IOB data, insulin history, glucose measurements, and a physiological model of glucose in response to insulin and other measurable factors, such as exercise and meal estimate and/or announcements. Additionally, at any time, the closed loop system in one embodiment of the invention is able to compute a desired bolus command that would result in the present and projected glucose of the user in a selected near future horizon falling within a specified nominal target, or one that optimizes the present and projected glucose with respect to some robust optimality criteria. This is a typical process involved in automatic closed looped systems that are model-based, such as a model-based approach that falls under the model predictive control (MPC) architecture.

When the system receives a temporary basal command, the closed loop system may, given the JOB, insulin history, glucose history, predicted glucose (in the near future horizon), and pre-programmed basal insulin delivery rate, compute a temporary basal amount and duration such that if the closed loop operation of the system terminates, the combination of the basal rate of that amount and the specified duration and the subsequent transition to the pre-programmed basal rate is such that the predicted glucose value of the user in the foreseeable future horizon will remain within a specified safe target. This safe target may be different from the specified nominal target value for the optimal calculation, in that it can be designed to be more conservative from a hazards prevention perspective.

Figure 3:
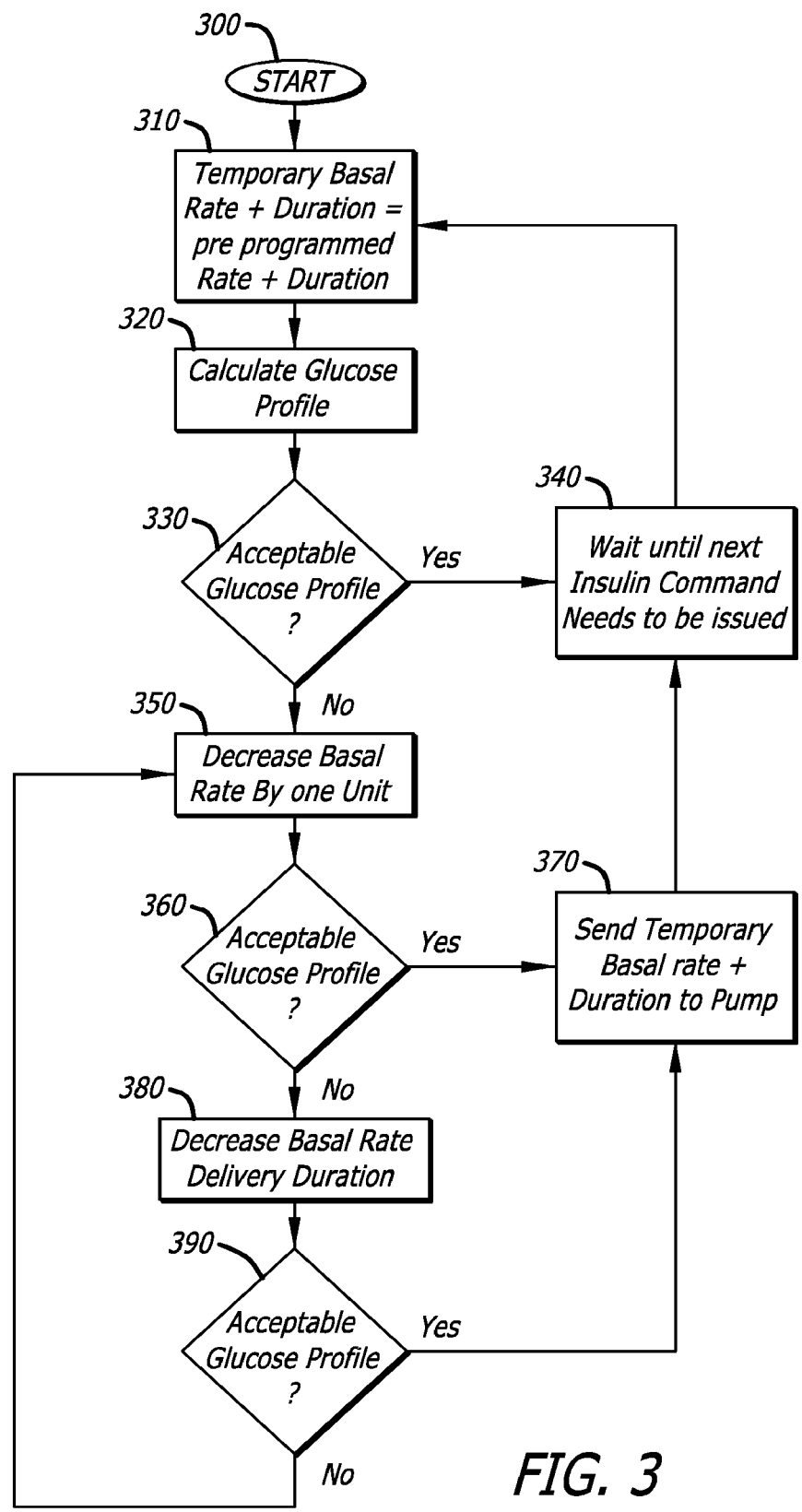
FIG. 3 is a block diagram illustrating an embodiment of the present invention.

An example of a process for determining a temporary basal rate of insulin delivery, along with the duration of that basal rate delivery, is illustrated by the diagram of FIG. 3. Appropriate software or hardware commands may be used to program the processor of the pump and/or controller to carry out the illustrated steps. Using a heuristic process, a glucose value may be predicted into the near future horizon under an assumption that the commanded bolus insulin delivery at present is followed by an immediate transfer to the programmed basal rate. In other words, the temporary basal rate candidate value calculated using the heuristic by the controller is identical to the pre-programmed basal rate.

Using this information as a starting point in box 310 as input into the selected model, a predicted glucose profile for a future time is calculated in box 320. If an acceptable predicted glucose profile results from this calculation in box 330, when there is no need to issue a temporary basal rate of any duration to maintain the user's glucose level within an acceptable range. When this is the case, the system waits until the next time an insulin command needs to be issued in box 340. When the next insulin command is determined to be needed, the processor begins at box 310, and once again carries out the process wherein glucose is predicted into the near future horizon as stated above.

If an acceptable predicted glucose profile does not result from the calculation carried out by the processor of the controller, the temporary basal insulin delivery rate is decreased by one value lower from the previous temporary basal rate candidate in box 350. The resolution of the basal rate for the particular pump and/or controller and/or glucose sensor determines the size of the reduction of basal rate that will be applied. This calculation may assume the maximum delivery duration allowable by the system.

If this assumption results in an acceptable predicted glucose profile in box 360, then a temporary basal insulin delivery command is sent using this basal rate and duration along with the nominal bolus command to the pump in box 370. The controller then waits until the next time an insulin command needs to be issued, and then restarts the process at box 310 again.

If an acceptable glucose profile is not calculated in box 360, the process keeps the same temporary basal rate as was used in box 350, and the decreases the duration of the basal rate delivery by an amount that is a function of system's resolution on command duration in box 380. If this calculation results in an acceptable predicted glucose profile in box 290, then a temporary basal command using this basal rate and duration along with the nominal bolus command is sent to the pump in box 370. Again, the controller waits until the next time an insulin command needs to be issued in box 340. When that time occurs, the process begins again box 310.

The iterative process described above is continued until the lowest allowable basal rate of insulin delivery is reached. If this assumption does not result in an acceptable predicted glucose profile, then the bolus command is reduced such that the combination of the reduced bolus rate and the temporary basal rate results in an acceptable predicted glucose profile.

If this is not possible, then an alert is sent to the user to take rescue carbohydrates or other actions that counteract the effect of excessive insulin.

The purpose of the above-described process is to add an additional safety calculation layer for the process control provided by automated closed-loop algorithms such that the closed-loop system computes two scenarios. First, the common scenario where insulin commands are issued and acted upon without interruption in the foreseeable future. This is normally computed by the automated closed-loop systems using model based approaches such as MPC. Second, the hazard-mitigated scenario where the sequence of insulin commands are abruptly interrupted after the latest command. The process set forth above addresses this scenario.

Using such a system, the embodiments of the present invention use model-based principles and available data to predict more than one scenario of insulin delivery such that when the periodic normal insulin command is interrupted, the system does not cause an unwanted hypoglycemic hazard. Avoiding unwanted hypoglycemia is important in providing proper control of glucose level in the diabetic user. The various embodiments of the invention provide better hazard mitigation against the risk of hypoglycemia due to a combination of insulin stacking (where a user already has an amount of insulin on board, but administers an additional bolus of insulin, often driving the user's glucose level towards hypoglycemia) and termination of closed-loop control. Utilizing a model-based approach improves the hazard mitigation caused by interruption of the automated closed-loop system, even though the interruption may have been accompanied by an alert/alarm or a temporary basal rate with a fixed duration.

In a CGM device such as the FreeStyle Navigator® Continuous Glucose Monitoring System that is distributed by Abbott Diabetes Care, there is a mute alarm feature that allows the user to mute the alarm when it is not easy for the user to respond to the alarm. Such alarms occur, for example, when the user's glucose level is either in the hyperglycemic range or, more importantly, in the hypoglycemic range.

For example, the user may choose to mute the alarm for the next two hours knowing that the user will be in a long meeting and does not want the alarm to disturb anyone. However, in the case of a low alarm signifying hypoglycemia, muting the alarm may lead to failure of the user to treat the hypoglycemic condition, which could be dangerous. The situation would be improved if at the time the user is muting the alarm, the system checks to determine the likelihood that the user may become hypoglycemic within the period of time that the alarm is muted. Generally, the system calculates a projected low-glucose level using IOB and real-time information to fine tune the projection and providing an alarm to indicate low glucose values. The problem with a persistent projected alarm, however, is the additional user annoyance associated with false positives. A user-initiated approach allows the user to define the time period that he wishes to have more precaution built into the control system as opposed to the system simply providing a persistent alarm to the user indicating that the controller has determined that some correction action is necessary, but at a time that a user is either unable or unwilling to take such action.

In one embodiment, the invention uses an overall strategy of potential low alarm detection to preempt pump control modification. Such a determination is useful during activities or events such as where the user goes to a long meeting or attends an event such as a movie, theatre, concert, or a long drive that may create a barrier from detecting and acting on a low-glucose level alarm. Another situation where the various embodiments of the invention are advantageous is where the user goes to bed at night and wishes to know whether a low glucose level alarm may sound during the night.

This embodiment of the invention includes a predictive alarm avoidance feature that is described hereafter. When the user foresees that he will be unavailable to act on an alarm in the near future, such as, for example, in the case where the user knows he will enter a meeting within the next 30 minutes, the user initiates the process of analyzing his current CGM glucose level and pump calculated IOB information to determine if the user's glucose level is likely be at in a range that the cause the device to produce an alarm during the meeting.

Using a controller that is programmed with appropriate software and hardware commands to carry out the functions required to perform the predictive alarm avoidance embodiment, the user enters the time horizon moving forward that he will be unavailable to take corrective actions if an alarm is presented. This entry is similar to the entry for the number of hours to mute an alarm in the current Freestyle Navigator® Continuous Glucose Monitoring System.

Based on the time horizon entered by the user, and other information found in the memory associated with the CGM and pump device, for example, but not limited to, the current CGM glucose level reading, the current IOB reading, the current bolus calculator parameters, and the current low and high reading settings, the processor calculates whether the user will be in one of three states in the future: a) a state where his glucose profile is adequate; b) in a carbohydrate deficient state, that is, a low glucose level state; and c) an insulin deficient state, that is, the user is in a hyperglycemic state during the time that he will not be able to make an adjustment to his pump. The following example illustrates this process.

Example 1

Assuming a user wishes to avoid an alarm where, and at the time he is commanding the controller to perform this calculation, the following values are pertinent to the calculation:

target threshold: 110 mg/dL,
high alarm threshold: 240 mg/dL,
lower alarm threshold: 70 mg/dL;
carbohydrate ratio: 1 unit of insulin for 15 grams of carb;
insulin sensitivity factor (ISF): 1 unit of insulin for 50 mg/dL; and
insulin action time: 5 hours.

In the case where the user will be unavailable or unwilling to take corrective action if he is presented with an alarm for the next three hours, the processor calculates a glucose level profile of the user utilizing the above factors to determine whether the user's glucose profile will stay in an acceptable range, or if the profile will result in either a hypo- or hyperglycemic state. In this case, with the above factors, the calculation reveals that the user would have an adequate glucose profile where the current CGM glucose value is 150 mg/dL and the current IOB is 1.1 units. Using methods well known by those in the art, the calculations carried out by the processor show that in five hours, the user's glucose level will decrease by 55 mg/dL (IOB*ISF), which is a glucose decline rate of 11 mg/dL per hour. Thus, during the three hours that the user will be unavailable or unwilling to take action to correct an alarm, the user's glucose level is estimated to be approximately 117 mg/dL (or, a 33 mg/dL decrease in glucose level from the user's current glucose level), which, for this user, is an acceptable glucose level.

Now considering the case where the user's current CGM glucose value is 150 mg/dL and the pump history (stored in the memory associated with the pump or controller) indicates a current IOB of 3.1 units. Using these starting values, the processor calculates that in five hours the user's glucose level will decrease by 155 mg/dL, which is a glucose decline rate of 31 mg/dL per hour. Thus, if the user is unavailable or unwilling to take corrective action in the next three hours, his glucose level will fall to around 57 mg/dL (a 93 mg/dL decrease in glucose level from the user's current glucose level), which is a carbohydrate deficient state.

Once the processor and controller knows that the user will be in a carbohydrate deficient state, the processor can recommend, for example, one or more of the following actions to the user using the display of the controller:

a) instruct the user to eat X grams of carbohydrates now or later to avoid the low glucose level, the value of X being calculated as X=(target minus future low)/ISF*carb ratio which is equal to (110 minus 57)/50*1.5=15.9 grams of carbohydrates; or b) instruct the user to reduce the basal rate of his insulin pump by using a temporary basal rate on the pump. The rate and duration of the temporary basal race is determined by the user using an interface on the device that can be interacted with by the user to cause the processor of the device to compute the temporary basal rate. For example, the controller may provide the user with the information he needs to program the processor of the device to reduce insulin delivery by X units per hour in the next three hours to i) stay within the target glucose level range, where X can be calculated as X=(target minus future low)/ISF/time horizon which is equal to (110 minus 57)/50/3 equals 0.354 units per hour (high reduction) or ii) maintain the user's glucose level above the low alarm threshold X=(low threshold minus future low)/ISF/time horizon equal (70 minus 57)/50/3 equals 0.087 units per hour (lower reduction);

c) the user may also be given the option of increasing the time horizon of the calculations, especially if the recommended reduced insulin amount is greater than the current basal rate, in order to bring about a more conservative reduction in the basal rate. For example, instead of reducing the amount of insulin delivered within the next three hours, the user may extend the time of insulin delivery to five hours.

If the user is watching a movie in a theatre, for example, the user may choose scenario a). If the user performs the calculation right before going to bed, or before taking a short nap, then he may choose scenario b) (assuming that the user's basal rate is greater than 0.087 units per hour or 0.35 per hour).

In a further example, a user's initial CGM glucose level is 280 mg/dL and the pump history indicates that the user's current IOB is 3.1 units. In this case, the processor calculates that in five hours, the user's glucose level will decrease by 155 mg/dL, which is a glucose level decline rate of 31 mg/dL per hour. With this glucose level decline rate, during the next three hours when the user is unavailable or unwilling to take corrective action, the user's glucose level is estimated by the processor to be around 187 mg/dL (a decrease of 93 mg/dL in glucose level from the user's current level), which could mean that the user will be in an insulin deficient state.

Given this calculation, the controller may also determine whether or not more insulin should be recommended to be taken by the user to avoid this possibly insulin deficient state this case, in five hours, based on the JOB, the user's glucose level can be estimated at 125 mg/dL, which a slightly above the user's target glucose level, so the controller and processor of the device may recommend slightly more insulin.

Alternatively, the device may recommend that the user does not need to do anything now or that he could choose to give himself a little more insulin (X units) using an extended bolus feature of the pump where:

$X$=the(predicted glucose level after insulin action time)−(the target glucose level)/ISF which is equal to 0.3 units, and Time duration=the user entered time horizon which is equal to three hours.

An embodiment of the controller of the present invention includes an appropriate User Interface (UI). This user interface is presented by the processor to the user and is formed by processor in accordance with appropriate software commands that have programmed the processor to operate accordingly. The user interface is user friendly to facilitate the user in making the appropriate pump changes. For example, the device should automatically initiate the UI process for temporary basal reduction in case b) and c) described above. Those skilled in the art will understand that the UI may take many different forms without departing from the scope of the present invention.

Because of the acute affect of hypoglycemia, a user is likely to use the above described process to avoid low-alarm occurrence. However, it is conceivable that a similar strategy can be used to avoid exposure to the hazards of hyperglycemia.

Not only can alarms be avoided using the various embodiments of the invention described above, but using a combined CGM and pump device, the actual state of low glucose level, or hypoglycemia, can be avoided. This further enhances the safety and usability of such CGM devices and insulin delivery pumps. Such an approach is also advantageous when compared to using a CGM based projected alarm feature alone which can result in annoying false positives and has much more limited future time projection. The described approach is also superior to muting an alarm to avoid the nuisance of repeated alarms and is also less annoying than a persistent projected low alarm. The user initiated, on-demand nature of the design and the pump control modification UI process integration affords better user control and allows more proactive user intervention to reduce glycemic variability. The embodiments of the invention described above are also advantageous because they can be used as a separate bedtime basal analysis to adjust the basal insulin rate slightly before going to bed. Such an adjustment is especially useful if the user if in a carbohydrate deficient state and does not wish to eat any food before going to bed, thus giving the user the option of reducing the basal rate of insulin delivery before going to bed.

Low glucose or hypoglycemia alarms are typically incorporated into continuous glucose monitoring systems to alert the user to potentially dangerous low glucose levels. For example, the low glucose alarm in the Freestyle Navigator® Continuous Glucose Monitoring System, distributed by Abbott Diabetes Care, is sounded when a user's glucose level falls below a user-defined low glucose threshold. This type of alarm may be subject to false triggering due to sensor signal anomalies such as sensor drop-outs, which are temporary and fully-recoverable signal attenuations believed to be associated with the application of pressure on the percutaneous sensor and/or transmitter as may occur during sleep.

The frequency of these false low-glucose alarms may be increased during closed-loop insulin delivery as the control algorithm will attempt to normalize glucose levels, increasing the percentage of time spent in or near the euglycemic range. Sensor drop outs that occur during hyperglycemia are less likely to trigger low glucose alarms because of these elevated glucose levels. In such a case, sensor drop outs may not sufficiently attenuate the sensor signal to elicit this response. However, if a user's glucose level is maintained closer to the euglycemic (acceptable, that is, neither hypo- nor hyperglycemic) range, as is expected during close-loop control, there is an increased likelihood that sensor drop-out will result in signal attenuation sufficient to cross the low glucose alarm threshold, which results in the presentation of an alarm condition to the user.

Under closed-loop conditions, where the presence of a closed-loop insulin delivery algorithm offers the additional hazard mitigation of the automatic reduction or suspension of insulin delivery based upon real-time glucose level measurements (or based upon the recent history of glucose readings), an alternative low glucose alarm approach may be preferred. In this embodiment, the low glucose level alarm is triggered when a low glucose threshold is exceeded for a clinically significant duration.

Various embodiments of such a delayed low glucose alarm are possible. For example, the alarm may be programmed to sound (1) after X minutes of continuous glucose measurements had been detected below some critical glucose value Y, where Xi=O; Yi=40 mg/dl; where X2=30; Y2=45 mg/dl; and where X3=120; Y3=60 mg/dl; or (2) After a continuous glucose measurement had been detected below some critical threshold A and had not recovered to either that critical threshold A or some intermediary threshold B within some specified duration (A' and B'); or (3) After some cumulative measure of time and duration below a low-glucose threshold, such as when the integral of some low glucose threshold minus the glucose profile exceeds a specified value before the continuous glucose level measurements have recovered to some specified value; or (4) After X minutes of closed loop insulin delivery rate (or total volume administered) below some specified threshold. In this case, insulin delivered is treated as a surrogate for measured glucose level due to the anticipated function of the control algorithm programmed into the software that is operating in the controller and/or pump.

Such an alarm approach is likely to reduce the frequency of false low glucose alarms by allowing for the possibility of the complete or partial recovery from the sensor-drop out to occur prior to the alarm presentation to the user. This loosening of alarm conditions is enabled by the increased safety to the user associated with the reduced or discontinued insulin infusion upon low continuous glucose values that is offered by a close-loop insulin level algorithm.

In another one embodiment of the invention, critical glucose level values are used to define the time allowed before the alarm sounds, resulting in a delayed alarm. For example, the time allowed value could be any appropriate function of glucose level, such as, for example only, and not limited to, a linear relationship.

For example, in one embodiment, the processor re-evaluates the time allowed before the alarm is sounded at every newly received glucose level measurement which is below some predefined or user set value. Using such an approach, if the glucose level is at 60 mg/dL (and previously above 60 mg/dL), then the time until the alarm sounded would be determined to be 60 minutes. One minute later, when the next glucose level value is calculated, the "time until alarm sound" may be calculated to be the lesser of 59 minutes, that is, 60 minutes decremented by one, and the time associated with a linear function; which may be, for example, 3 minutes for every 1 mg/dL that the glucose value is below 60 mg/dL. Thus, if the second glucose value is 55 mg/dL, a decrease in glucose of 15 mg/dL, then the new "time until alarm sound" will be 45 minutes (60 minutes-(3 minutes per mg/dL-.times.15 mg/dL). This determination is repeated for every glucose value received until the alarm sounds or the user's glucose level is greater than 60 mg/dL. Various approaches to this problem may be used individually or in combination in order to minimize false hypoglycemic alarms due to drop outs.

Yet another embodiment of the present invention utilizes model based variable risk determinations to calculate an alarm delay to prevent the annunciation of false alarms, while still providing acceptable protection against a user entering an unacceptable glucose level condition. When CGM systems are used by persons with good glucose control, either by fully manual means, fully automated closed loop operation, or any hybrid means in between, the users glucose will typically be controlled much closer to the euglycemia range than would otherwise occur. This close control, coupled with the expected error distribution of CGM measurements, means that there will be an increased likelihood of CGM values close to or below the hypoglycemia limit. In addition to CGM calibration error, certain CGM signal distortion phenomena such as night time drop-outs also increase the likelihood of an underreported glucose value by the CGM system.

The combination of the three aforementioned factors interacts with standard hypoglycemia detectors to produce a higher incidence of false alarm rates. One embodiment of the invention designed to deal with this problem has been described above. Other approaches are also possible, and intended to be within the scope of the present invention, such as raising the importance and persistency of alarms depending on the length of time the alarm condition has existed without action by the user. Such approaches allow for false hypoglycemic alarms due to a combination of the three aforementioned factors to be minimized.

There will, however, be instances where the patient's physiology and activity temporally pushes their glucose profile out of euglycemia and into either a higher likelihood of hypoglycemia or hyperglycemia. Examples of events where hyperglycemia is more likely would be after exercise, of after a meal where the user failed to receive an insufficient prandial bolus of insulin.

If the user has a system including a CGM and an insulin delivery pump, information from the devices can be pooled or shared, and a model-based monitoring system can be used to modify the alarm mechanism to more efficiently minimize false alarms without imposing unnecessary risk to the patient. Using the information available from the CGM glucose monitor and insulin delivery system, as well as other information entered by the user whenever available (for example, the amount of exercise, state of health, and the like), a model-based system defined by appropriate software commands running on a processor of a controller can perform a prediction of glucose in terms of best estimate and upper/lower bounds for the present time up to a finite horizon in the future. Such a system can be achieved, for example, by implementing the user's model in the form of a Kalman Filter framework, where both the best estimate and variance of each model state is estimated, predicted, and modeled.

Using the present-to-near-future best estimate and bounds, the user's most likely temporal range can be inferred. For example, assume the hypoglycemic detection mechanism of the programming of the controller or pump has 3 levels: 1) wait 30 minutes when the CGM determined glucose level crosses a 60 mg/dL threshold; 2) wait 15 minutes when the CGM determined glucose level crosses a 50 mg/dL threshold, and 3) alarm immediately when the CGM glucose level crosses a 45 mg/dL threshold. A Kalman framework may be used to determine the likelihood for a predicted future glucose level, given the user's current CGM glucose level and other insulin delivery history. This mechanism is implemented "as is" when the model's temporal glucose range suggests the lowest hypoglycemic likelihood. As the likelihood reaches the middle-range risk, then the mechanism is implemented with a 50% shortening of the pre-set delay for sounding the hypoglycemic alarm. For example, the detection levels set forth above may be modified as follows: 1') wait 15 minutes when the CGM glucose level crosses the 60 mg/dL threshold; 2') wait 7.5 minutes when the CGM glucose level crosses the 50 mg/dL threshold, and 3') alarm immediately when the CGM glucose level crosses the 45 mg/dL threshold. When the highest risk of hypoglycemic likelihood is determined, the alarm threshold has 0 delay.

In another embodiment, the same mechanism is implemented, that is: a) wait 30 minutes when the CGM glucose level crosses the 60 mg/dL threshold; b) wait 15 minutes when the CGM glucose level crosses the 50 gm/dL threshold; and 3) alarm immediately when the CGM glucose level crosses the 45 mg/dL threshold) when the model' temporal glucose range suggests the lowest hypoglycemic likelihood. In the middle-range risk, the same delays are retained, but the threshold values are increased, such as, for example: a') wait 30 minutes when the CGM glucose level crosses the 60+5 mg/dL threshold; b') wait 15 minutes when the CGM glucose level crosses the 50+5 mg/dL threshold; and c') alarm immediately when the CGM glucose level crosses the crosses 45+5 mg/dL threshold.

In yet another embodiment, a hybrid of the two previous embodiments may be used. In such an embodiment, both the threshold values and the delay time may be adjusted based on the temporal glucose range determined by the model.

The same types of mechanisms may be applied to hyperglycemia detection, with the tiered thresholds increasing in the order of threshold values. For example, where the CGM glucose level crosses a 180 mg/dL threshold the longest delay time is implemented; where the CGM glucose level crosses a 200 mg/dL threshold, a shorter delay time is implemented before sounding an alarm; and where the CGM glucose level crosses a 220 gm/dL threshold, an even shorter delay time is implemented, up to a maximum threshold with a zero delay time.

While several specific embodiments of the invention have been illustrated and described, it will be apparent that various modifications can be made without departing from the spirit and scope of the invention. Accordingly, it is not intended that the invention be limited, except as by the appended claims.

What is claimed is:

1. A method for providing notifications related to a predicted glucose level for a user, comprising:
    detecting a glucose level of the user using an analyte sensor;
    determining a predicted glucose level for a future time period during which the user is unable to take corrective action;
    generating, by a user interface, one or more notifications related to the predicted glucose level for the future time period, wherein the one or more notifications comprises a corrective action to adjust the glucose level of the user; and
    receiving a selection by the user to implement the corrective action.

2. The method of claim 1, wherein the one or more notifications are generated based upon the predicted glucose level crossing one or more predetermined analyte thresholds.

3. The method of claim 2, wherein the predetermined glucose threshold comprises a low glucose level.

4. The method of claim 2, wherein the one or more predetermined analyte thresholds are received prophylactically in preparation of the period during which the user is unable to take corrective action.

5. The method of claim 1, wherein the one or more notifications comprise a recommendation to ingest an amount of carbohydrates.

6. The method of claim 5, wherein the amount of carbohydrates is calculated based on the detected glucose level.

7. The method of claim 1, wherein the one or more notifications comprise a recommendation to reduce a basal rate of a medication delivery device of the user.

8. The method of claim 1, wherein the one or more notifications comprise a recommendation to increase a time horizon of a medication delivery device of the user.

9. The method of claim 1, further comprising implementing the corrective action to prevent the user's glucose level from crossing one or more predetermined analyte thresholds during the future period.

10. The method of claim 1, further comprising calculating a glucose level profile of the user based on the detected glucose level of the user and one or more parameters, wherein the predicted glucose level is determined based upon the calculated glucose profile.

11. The method of claim 1, wherein the one or more notifications is displayed on the user interface.

12. The method of claim 1, further comprising, receiving the future time period during which the user is unable to take corrective action and wherein the generated one or more notifications are provided before a beginning of the future time period during which the user is unable to take corrective action.

13. The method of claim 12, wherein the received futured time period during which the user is unable to take corrective action is input into the user interface.

14. An analyte monitoring system for providing notifications related to a predicted glucose level for a user, comprising:
    an analyte sensor when at least partially inserted into interstitial fluid of the user is configured to detect a glucose level of the user;
    a user interface;
    a processor operably coupled to the analyte sensor; and
    a memory operably coupled to the processor, wherein the memory includes instructions stored therein that, when executed by the processor, cause the processor to:
        detect the glucose level using the analyte sensor;
        determine the predicted glucose level for a future time period during which the user is unable to take corrective action;

generate, by the user interface, one or more notifications related to the predicted glucose level for the future time period, wherein the one or more notifications comprises a corrective action to adjust the glucose level of the user; and receive a selection by the user to implement the corrective action.

15. The system of claim 14, wherein the analyte sensor is a glucose sensor.

16. The system of claim 14, wherein the one or more notifications are generated based upon the predicted glucose level crossing one or more predetermined glucose thresholds.

17. The system of claim 16, wherein the predetermined glucose threshold comprises a low glucose level.

18. The system of claim 14, wherein the one or more notifications comprise a recommendation to ingest an amount of carbohydrates.

19. The system of claim 18, wherein the amount of carbohydrates is calculated based on the detected glucose level.

20. The system of claim 14, wherein the one or more notifications comprise a recommendation to reduce a basal rate of a medication delivery device of the user.

21. The system of claim 14, wherein the one or more notifications comprise a recommendation to increase a time horizon of a medication delivery device of the user.

22. The system of claim 14, wherein the system is further in communication with a medication delivery device.

23. The system of claim 14, the memory further comprises instructions to calculate a glucose level profile of the user based on the detected glucose level of the user and one or more parameters, wherein the predicted glucose level is determined based upon the calculated glucose profile.

24. The system of claim 14, wherein the one or more notifications is displayed on the user interface.

25. The system of claim 14, the instructions further comprising, receive the future time period during which the user is unable to take corrective action and wherein the generated one or more notifications are provided before a beginning of the future time period during which the user is unable to take corrective action.

26. The system of claim 25, wherein the received futured time period during which the user is unable to take corrective action is input into the user interface.

* * * * *